(12) United States Patent
Zhang et al.

(10) Patent No.: US 8,758,260 B2
(45) Date of Patent: *Jun. 24, 2014

(54) ISCHEMIA DETECTION USING A HEART SOUND SENSOR

(75) Inventors: Yi Zhang, Plymouth, MN (US); Richard Fogoros, Pittsburg, PA (US); Carlos Haro, Stevenson Ranch, CA (US); Yousufali Dalal, Irvine, CA (US); Marina V. Brockway, Shoreview, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 330 days.

This patent is subject to a terminal disclaimer.

(21) Appl. No.: 13/231,152

(22) Filed: Sep. 13, 2011

(65) Prior Publication Data

US 2012/0004565 A1    Jan. 5, 2012

Related U.S. Application Data

(60) Continuation of application No. 12/510,962, filed on Jul. 28, 2009, now Pat. No. 8,034,000, which is a division of application No. 11/148,107, filed on Jun. 8, 2005, now Pat. No. 7,922,669.

(51) Int. Cl.
*A61B 5/04*    (2006.01)

(52) U.S. Cl.
USPC .......................................................... 600/528

(58) Field of Classification Search
USPC .......................................................... 600/528
See application file for complete search history.

(56) References Cited

U.S. PATENT DOCUMENTS

| | | | |
|---|---|---|---|
| 3,773,033 | A | 11/1973 | Rodbard et al. |
| 3,799,147 | A | 3/1974 | Adolph et al. |
| 4,094,308 | A | 6/1978 | Cormier |
| 4,173,971 | A | 11/1979 | Karz |
| 4,220,160 | A | 9/1980 | Kimball et al. |

(Continued)

FOREIGN PATENT DOCUMENTS

| | | |
|---|---|---|
| CA | 2459408 A1 | 3/2003 |
| EP | 297675 A1 | 1/1989 |

(Continued)

OTHER PUBLICATIONS

U.S. Appl. No. 10/138,046, Non Final Office Action mailed Jun. 29, 2005, 14 pgs.

(Continued)

*Primary Examiner* — Eric D. Bertram
(74) *Attorney, Agent, or Firm* — Schwegman, Lundberg & Woessner, P. A.

(57) ABSTRACT

A system comprising an implantable medical device (IMD) includes an implantable heart sound sensor to produce an electrical signal representative of at least one heart sound. The heart sound is associated with mechanical activity of a patient's heart. Additionally, the IMD includes a heart sound sensor interface circuit coupled to the heart sound sensor to produce a heart sound signal, and a signal analyzer circuit coupled to the heart sound sensor interface circuit. The signal analyzer circuit measures a baseline heart sound signal, and deems that an ischemic event has occurred using, among other things, a measured subsequent change in the heart sound signal from the established baseline heart sound signal.

20 Claims, 8 Drawing Sheets

(56) References Cited

U.S. PATENT DOCUMENTS

| | | |
|---|---|---|
| 4,289,141 A | 9/1981 | Cormier |
| 4,291,699 A | 9/1981 | Geddes et al. |
| 4,354,497 A | 10/1982 | Kahn |
| 4,428,378 A | 1/1984 | Anderson et al. |
| 4,428,380 A | 1/1984 | Wong et al. |
| 4,446,872 A | 5/1984 | Marsoner et al. |
| 4,548,204 A | 10/1985 | Groch et al. |
| 4,586,514 A | 5/1986 | Schlager et al. |
| 4,628,939 A | 12/1986 | Little et al. |
| 4,649,930 A | 3/1987 | Groch et al. |
| 4,674,518 A | 6/1987 | Salo |
| 4,686,987 A | 8/1987 | Salo et al. |
| 4,702,253 A | 10/1987 | Nappholz et al. |
| 4,763,646 A | 8/1988 | Lekholm |
| 4,773,401 A | 9/1988 | Citak et al. |
| 4,777,960 A | 10/1988 | Berger et al. |
| 4,796,639 A | 1/1989 | Snow et al. |
| 4,830,006 A | 5/1989 | Haluska et al. |
| 4,872,459 A | 10/1989 | Pless et al. |
| 4,880,005 A | 11/1989 | Pless et al. |
| 4,905,706 A | 3/1990 | Duff et al. |
| 4,915,113 A | 4/1990 | Holman |
| 4,945,909 A | 8/1990 | Fearnot et al. |
| 4,967,760 A | 11/1990 | Bennett et al. |
| 4,981,139 A | 1/1991 | Pfohl |
| 4,989,611 A | 2/1991 | Zanetti et al. |
| 5,007,427 A | 4/1991 | Suzuki et al. |
| 5,010,889 A | 4/1991 | Bredesen et al. |
| 5,012,815 A | 5/1991 | Bennett, Jr. et al. |
| 5,014,698 A | 5/1991 | Cohen |
| 5,025,809 A | 6/1991 | Johnson et al. |
| 5,040,533 A | 8/1991 | Fearnot |
| 5,072,458 A | 12/1991 | Suzuki |
| 5,111,818 A | 5/1992 | Suzuki et al. |
| 5,113,869 A | 5/1992 | Nappholz et al. |
| 5,135,004 A | 8/1992 | Adams et al. |
| 5,137,019 A | 8/1992 | Pederson et al. |
| 5,156,149 A | 10/1992 | Hudrlik |
| 5,158,079 A | 10/1992 | Adams et al. |
| 5,159,932 A | 11/1992 | Zanetti et al. |
| 5,168,869 A | 12/1992 | Chirife |
| 5,174,289 A | 12/1992 | Cohen |
| 5,179,947 A | 1/1993 | Meyerson et al. |
| 5,190,035 A | 3/1993 | Salo et al. |
| 5,199,428 A | 4/1993 | Obel et al. |
| 5,205,283 A | 4/1993 | Olson |
| 5,218,969 A | 6/1993 | Bredesen et al. |
| 5,233,985 A | 8/1993 | Hudrlik |
| 5,267,560 A | 12/1993 | Cohen |
| 5,282,840 A | 2/1994 | Hudrlik et al. |
| 5,284,136 A | 2/1994 | Hauck et al. |
| 5,292,341 A | 3/1994 | Snell |
| 5,301,679 A | 4/1994 | Taylor |
| 5,305,745 A | 4/1994 | Zacouto |
| 5,313,953 A | 5/1994 | Yomtov et al. |
| 5,321,618 A | 6/1994 | Gessman |
| 5,330,511 A | 7/1994 | Boute |
| 5,331,768 A | 7/1994 | Takeuchi |
| 5,331,966 A | 7/1994 | Bennett et al. |
| 5,334,221 A | 8/1994 | Bardy |
| 5,334,222 A | 8/1994 | Salo et al. |
| 5,337,752 A | 8/1994 | Reeves |
| 5,365,932 A | 11/1994 | Greenhut |
| 5,370,665 A | 12/1994 | Hudrlik |
| 5,376,106 A | 12/1994 | Stahmann et al. |
| 5,391,190 A | 2/1995 | Pederson et al. |
| 5,411,531 A | 5/1995 | Hill et al. |
| 5,417,717 A | 5/1995 | Salo et al. |
| 5,472,453 A | 12/1995 | Alt |
| 5,487,752 A | 1/1996 | Salo et al. |
| 5,496,361 A | 3/1996 | Moberg et al. |
| 5,514,161 A | 5/1996 | Limousin |
| 5,514,163 A | 5/1996 | Markowitz et al. |
| 5,527,347 A | 6/1996 | Shelton et al. |
| 5,531,768 A | 7/1996 | Alferness |
| 5,534,016 A | 7/1996 | Boute |
| 5,544,661 A | 8/1996 | Davis et al. |
| 5,549,650 A | 8/1996 | Bornzin et al. |
| 5,554,177 A | 9/1996 | Kieval et al. |
| 5,584,867 A | 12/1996 | Limousin et al. |
| 5,584,868 A | 12/1996 | Salo et al. |
| 5,593,431 A | 1/1997 | Sheldon |
| 5,609,612 A | 3/1997 | Plicchi et al. |
| 5,620,472 A | 4/1997 | Rahbari |
| 5,626,620 A | 5/1997 | Kieval et al. |
| 5,626,623 A | 5/1997 | Kieval et al. |
| 5,628,777 A | 5/1997 | Moberg et al. |
| 5,674,256 A | 10/1997 | Carlson |
| 5,674,259 A | 10/1997 | Gray |
| 5,683,429 A | 11/1997 | Mehra |
| 5,685,317 A | 11/1997 | Sjostrom |
| 5,687,738 A | 11/1997 | Shapiro et al. |
| 5,693,075 A | 12/1997 | Plicchi et al. |
| 5,697,375 A | 12/1997 | Hickey |
| 5,697,959 A | 12/1997 | Poore |
| 5,700,283 A | 12/1997 | Salo |
| 5,704,365 A | 1/1998 | Albrecht et al. |
| 5,713,355 A | 2/1998 | Richardson et al. |
| 5,713,930 A | 2/1998 | van der Veen et al. |
| 5,716,382 A | 2/1998 | Snell |
| 5,716,383 A | 2/1998 | Kieval et al. |
| 5,720,771 A | 2/1998 | Snell |
| 5,722,999 A | 3/1998 | Snell |
| 5,724,985 A | 3/1998 | Snell et al. |
| 5,725,562 A | 3/1998 | Sheldon |
| 5,749,906 A | 5/1998 | Kieval et al. |
| 5,759,199 A | 6/1998 | Snell et al. |
| 5,792,195 A | 8/1998 | Carlson et al. |
| 5,797,970 A | 8/1998 | Pouvreau |
| 5,800,471 A | 9/1998 | Baumann |
| 5,800,473 A | 9/1998 | Faisandier |
| 5,824,019 A | 10/1998 | Rueter et al. |
| 5,836,987 A | 11/1998 | Baumann et al. |
| 5,860,933 A | 1/1999 | Don Michael |
| 5,911,738 A | 6/1999 | Sikorski et al. |
| 5,919,209 A | 7/1999 | Schouten |
| 5,935,081 A | 8/1999 | Kadhiresan |
| 5,935,160 A | 8/1999 | Auricchio et al. |
| 5,951,593 A | 9/1999 | Lu et al. |
| 5,974,340 A | 10/1999 | Kadhiresan |
| 5,987,352 A | 11/1999 | Klein et al. |
| 5,991,657 A | 11/1999 | Kim |
| 5,991,661 A | 11/1999 | Park et al. |
| 6,002,777 A | 12/1999 | Grasfield et al. |
| 6,009,349 A | 12/1999 | Mouchawar et al. |
| 6,015,388 A | 1/2000 | Sackner et al. |
| 6,021,350 A | 2/2000 | Mathson |
| 6,022,322 A | 2/2000 | Prutchi |
| 6,022,963 A | 2/2000 | McGall et al. |
| 6,026,324 A | 2/2000 | Carlson |
| 6,038,483 A | 3/2000 | KenKnight et al. |
| 6,044,297 A | 3/2000 | Sheldon et al. |
| 6,044,298 A | 3/2000 | Salo et al. |
| 6,044,299 A | 3/2000 | Nilsson |
| 6,045,513 A | 4/2000 | Stone et al. |
| 6,048,319 A | 4/2000 | Hudgins et al. |
| 6,053,872 A | 4/2000 | Mohler |
| 6,058,329 A | 5/2000 | Salo et al. |
| 6,064,910 A | 5/2000 | Andersson et al. |
| 6,070,101 A | 5/2000 | Struble et al. |
| 6,076,015 A | 6/2000 | Hartley et al. |
| 6,077,227 A | 6/2000 | Miesel |
| 6,104,949 A | 8/2000 | Pitts et al. |
| 6,108,577 A | 8/2000 | Benser |
| 6,112,117 A | 8/2000 | KenKnight et al. |
| 6,115,628 A | 9/2000 | Stadler et al. |
| 6,115,630 A | 9/2000 | Stadler et al. |
| 6,128,526 A | 10/2000 | Stadler et al. |
| 6,144,880 A | 11/2000 | Ding et al. |
| 6,151,524 A | 11/2000 | Krig et al. |
| 6,152,884 A | 11/2000 | Bjorgaas |
| 6,152,955 A | 11/2000 | KenKnight et al. |
| 6,161,042 A | 12/2000 | Hartley et al. |
| 6,179,865 B1 | 1/2001 | Hsu et al. |

(56) References Cited

U.S. PATENT DOCUMENTS

| | | |
|---|---|---|
| 6,190,324 B1 | 2/2001 | Kieval et al. |
| 6,193,668 B1 | 2/2001 | Chassaing et al. |
| 6,208,900 B1 | 3/2001 | Ecker et al. |
| 6,208,901 B1 | 3/2001 | Hartung |
| 6,223,082 B1 | 4/2001 | Bakels et al. |
| 6,230,059 B1 | 5/2001 | Duffin |
| 6,236,882 B1 | 5/2001 | Lee et al. |
| 6,240,317 B1 | 5/2001 | Villaseca et al. |
| 6,251,126 B1 | 6/2001 | Ottenhoff et al. |
| 6,256,538 B1 | 7/2001 | Ekwall |
| 6,264,611 B1 | 7/2001 | Ishikawa et al. |
| 6,269,269 B1 | 7/2001 | Ottenhoff et al. |
| 6,269,396 B1 | 7/2001 | Shah et al. |
| 6,272,377 B1 | 8/2001 | Sweeney et al. |
| 6,272,379 B1 | 8/2001 | Fischell et al. |
| 6,273,856 B1 | 8/2001 | Sun et al. |
| 6,275,727 B1 | 8/2001 | Hopper et al. |
| 6,278,894 B1 | 8/2001 | Salo et al. |
| 6,280,389 B1 | 8/2001 | Ding et al. |
| 6,285,898 B1 | 9/2001 | Ben-Haim |
| 6,298,269 B1 | 10/2001 | Sweeney |
| 6,304,773 B1 | 10/2001 | Taylor et al. |
| 6,311,089 B1 | 10/2001 | Mann et al. |
| 6,312,378 B1 | 11/2001 | Bardy |
| 6,314,323 B1 | 11/2001 | Ekwall |
| 6,324,421 B1 | 11/2001 | Stadler et al. |
| 6,327,622 B1 | 12/2001 | Jindal et al. |
| 6,336,903 B1 | 1/2002 | Bardy |
| 6,347,245 B1 | 2/2002 | Lee et al. |
| 6,351,672 B1 | 2/2002 | Park et al. |
| 6,351,673 B1 | 2/2002 | Ding et al. |
| 6,351,675 B1 | 2/2002 | Tholen et al. |
| 6,360,127 B1 | 3/2002 | Ding et al. |
| 6,361,522 B1 | 3/2002 | Scheiner et al. |
| 6,366,811 B1 | 4/2002 | Carlson |
| 6,368,283 B1 | 4/2002 | Xu et al. |
| 6,368,284 B1 | 4/2002 | Bardy |
| 6,370,424 B1 | 4/2002 | Prutchi |
| 6,381,493 B1 | 4/2002 | Stadler et al. |
| 6,397,100 B2 | 5/2002 | Stadler et al. |
| 6,398,728 B1 | 6/2002 | Bardy |
| 6,408,208 B1 | 6/2002 | Sun |
| 6,409,675 B1 | 6/2002 | Turcott |
| 6,411,840 B1 | 6/2002 | Bardy |
| 6,411,847 B1 | 6/2002 | Mower |
| 6,415,033 B1 | 7/2002 | Halleck et al. |
| 6,423,705 B1 | 7/2002 | Tracey et al. |
| 6,430,439 B1 | 8/2002 | Wentkowski et al. |
| 6,438,421 B1 | 8/2002 | Stahmann et al. |
| 6,440,066 B1 | 8/2002 | Bardy |
| 6,440,082 B1 | 8/2002 | Joo et al. |
| 6,442,433 B1 | 8/2002 | Linberg |
| 6,449,510 B1 | 9/2002 | Albers et al. |
| 6,459,929 B1 | 10/2002 | Hopper et al. |
| 6,463,326 B1 | 10/2002 | Hartley et al. |
| 6,466,821 B1 | 10/2002 | Pianca et al. |
| 6,477,406 B1 | 11/2002 | Turcott |
| 6,478,746 B2 | 11/2002 | Chassaing et al. |
| 6,480,733 B1 | 11/2002 | Turcott |
| 6,480,742 B2 | 11/2002 | Stahmann et al. |
| 6,491,639 B1 | 12/2002 | Turcott |
| 6,496,715 B1 | 12/2002 | Lee et al. |
| 6,496,721 B1 | 12/2002 | Yonce |
| 6,501,983 B1 | 12/2002 | Natarajan et al. |
| 6,507,756 B1 | 1/2003 | Heynen et al. |
| 6,512,952 B2 | 1/2003 | Stahmann et al. |
| 6,520,924 B2 | 2/2003 | Lee |
| 6,522,921 B2 | 2/2003 | Stahmann et al. |
| 6,522,923 B1 | 2/2003 | Turcott |
| 6,527,729 B1 | 3/2003 | Turcott |
| 6,531,907 B2 | 3/2003 | Dooley et al. |
| 6,542,775 B2 | 4/2003 | Ding et al. |
| 6,553,258 B2 | 4/2003 | Stahmann et al. |
| RE38,119 E | 5/2003 | Mower |
| 6,567,700 B1 | 5/2003 | Turcott et al. |
| 6,575,916 B2 | 6/2003 | Halleck et al. |
| 6,610,713 B2 | 8/2003 | Tracey |
| 6,625,493 B2 | 9/2003 | Kroll et al. |
| 6,626,842 B2 | 9/2003 | Oka |
| 6,643,548 B1 * | 11/2003 | Mai et al. ......................... 607/17 |
| 6,645,145 B1 | 11/2003 | Dreschel et al. |
| 6,650,940 B1 | 11/2003 | Zhu et al. |
| 6,658,292 B2 | 12/2003 | Kroll et al. |
| 6,665,564 B2 | 12/2003 | Lincoln et al. |
| 6,666,826 B2 | 12/2003 | Salo et al. |
| 6,684,103 B2 | 1/2004 | Ding et al. |
| 6,702,720 B2 | 3/2004 | Dardik |
| 6,719,701 B2 | 4/2004 | Lade |
| 6,733,464 B2 | 5/2004 | Olbrich et al. |
| 6,741,886 B2 | 5/2004 | Yonce |
| 6,752,765 B1 | 6/2004 | Jensen et al. |
| 6,788,970 B1 | 9/2004 | Park et al. |
| 6,792,308 B2 | 9/2004 | Corbucci |
| 6,795,732 B2 | 9/2004 | Stadler et al. |
| 6,804,558 B2 | 10/2004 | Haller et al. |
| 6,810,284 B1 | 10/2004 | Bradley |
| 6,810,287 B2 | 10/2004 | Zhu et al. |
| 6,824,519 B2 | 11/2004 | Narimatsu et al. |
| 6,827,690 B2 | 12/2004 | Bardy |
| 6,830,548 B2 | 12/2004 | Bonnet et al. |
| 6,838,471 B2 | 1/2005 | Tracey |
| 6,845,263 B2 | 1/2005 | Kawaguchi |
| 6,845,267 B2 | 1/2005 | Harrison et al. |
| 6,865,420 B1 | 3/2005 | Kroll |
| 6,868,346 B2 | 3/2005 | Larson et al. |
| 6,885,889 B2 | 4/2005 | Chinchoy |
| 6,892,095 B2 | 5/2005 | Salo |
| 6,913,577 B2 | 7/2005 | Bardy |
| 6,915,160 B2 | 7/2005 | Auricchio et al. |
| 6,937,899 B2 | 8/2005 | Sheldon et al. |
| 6,942,622 B1 | 9/2005 | Turcott |
| 6,949,075 B2 | 9/2005 | Hatlestad et al. |
| 6,963,777 B2 | 11/2005 | Lincoln et al. |
| 6,973,349 B2 | 12/2005 | Salo |
| 6,980,851 B2 | 12/2005 | Zhu et al. |
| 7,010,342 B2 | 3/2006 | Galen et al. |
| 7,010,345 B2 | 3/2006 | Hill et al. |
| 7,020,521 B1 | 3/2006 | Brewer et al. |
| 7,039,462 B2 | 5/2006 | Pastore et al. |
| 7,043,305 B2 | 5/2006 | Kenknight et al. |
| 7,052,466 B2 | 5/2006 | Scheiner et al. |
| 7,065,397 B2 | 6/2006 | Galen et al. |
| 7,069,070 B2 | 6/2006 | Carlson et al. |
| 7,072,708 B1 | 7/2006 | Andersen et al. |
| 7,072,711 B2 | 7/2006 | Girouard et al. |
| 7,074,195 B2 | 7/2006 | Nelson et al. |
| 7,079,895 B2 | 7/2006 | Verbeek et al. |
| 7,096,060 B2 | 8/2006 | Arand et al. |
| 7,110,804 B2 | 9/2006 | Baumer et al. |
| 7,110,817 B2 | 9/2006 | Yu et al. |
| 7,113,825 B2 | 9/2006 | Pastore et al. |
| 7,115,096 B2 | 10/2006 | Siejko et al. |
| 7,123,962 B2 | 10/2006 | Siejko et al. |
| 7,127,290 B2 | 10/2006 | Girouard et al. |
| 7,139,609 B1 | 11/2006 | Min et al. |
| 7,158,830 B2 | 1/2007 | Yu et al. |
| 7,171,258 B2 | 1/2007 | Goode |
| 7,174,203 B2 | 2/2007 | Arand et al. |
| 7,177,685 B2 | 2/2007 | Lincoln et al. |
| 7,194,306 B1 | 3/2007 | Turcott |
| 7,209,786 B2 | 4/2007 | Brockway et al. |
| 7,215,992 B2 | 5/2007 | Stahmann et al. |
| 7,215,997 B2 | 5/2007 | Yu et al. |
| 7,226,422 B2 | 6/2007 | Hatlestad et al. |
| 7,248,923 B2 | 7/2007 | Maile et al. |
| 7,260,429 B2 | 8/2007 | Siejko et al. |
| 7,299,087 B2 | 11/2007 | Bardy |
| 7,340,303 B2 | 3/2008 | Zhu |
| 7,364,547 B2 | 4/2008 | Stahmann et al. |
| 7,366,568 B2 | 4/2008 | Pastore et al. |
| 7,387,610 B2 | 6/2008 | Stahmann et al. |
| 7,400,928 B2 | 7/2008 | Hatlestad |
| 7,403,813 B1 | 7/2008 | Farazi et al. |
| 7,424,321 B2 | 9/2008 | Wariar et al. |

(56) References Cited

U.S. PATENT DOCUMENTS

| | | |
|---|---|---|
| 7,431,699 B2 | 10/2008 | Siejko et al. |
| 7,460,906 B2 | 12/2008 | Libbus |
| 7,479,112 B2 | 1/2009 | Sweeney et al. |
| 7,480,528 B2 | 1/2009 | Brockway et al. |
| 7,486,991 B2 | 2/2009 | Libbus et al. |
| 7,493,162 B2 | 2/2009 | Girouard et al. |
| 7,559,901 B2 | 7/2009 | Maile et al. |
| 7,567,836 B2 | 7/2009 | Zhang |
| 7,582,061 B2 | 9/2009 | Li et al. |
| 7,585,279 B2 | 9/2009 | Carlson et al. |
| 7,662,101 B2 | 2/2010 | Lee et al. |
| 7,662,104 B2 | 2/2010 | Krzysztof et al. |
| 7,668,594 B2 | 2/2010 | Marina et al. |
| 7,713,213 B2 | 5/2010 | Siejko et al. |
| 7,736,319 B2 | 6/2010 | Patangay et al. |
| 7,751,890 B2 | 7/2010 | McCabe et al. |
| 7,780,606 B2 | 8/2010 | Carlson et al. |
| 7,844,334 B2 | 11/2010 | Maile et al. |
| 7,853,327 B2 | 12/2010 | Patangay et al. |
| 7,885,710 B2 | 2/2011 | Sih et al. |
| 7,917,210 B2 | 3/2011 | Baynham et al. |
| 7,922,669 B2 | 4/2011 | Zhang et al. |
| 7,938,781 B2 | 5/2011 | Carlson et al. |
| 7,951,087 B2 | 5/2011 | Siejko et al. |
| 7,972,275 B2 | 7/2011 | Siejko et al. |
| 8,108,034 B2 | 1/2012 | Patangay et al. |
| 8,211,033 B2 | 7/2012 | Siejko et al. |
| 8,340,764 B2 | 12/2012 | Baynham et al. |
| 8,396,552 B2 | 3/2013 | Baynham et al. |
| 8,500,650 B2 | 8/2013 | Siejko et al. |
| 8,636,669 B2 | 1/2014 | Siejko et al. |
| 2001/0007053 A1 | 7/2001 | Bardy |
| 2001/0012955 A1 | 8/2001 | Goedeke et al. |
| 2001/0047125 A1 | 11/2001 | Quy |
| 2002/0001390 A1 | 1/2002 | Kawaguchi |
| 2002/0002389 A1 | 1/2002 | Bradley et al. |
| 2002/0016548 A1 | 2/2002 | Stadler et al. |
| 2002/0016550 A1 | 2/2002 | Sweeney et al. |
| 2002/0019586 A1 | 2/2002 | Teller et al. |
| 2002/0026103 A1 | 2/2002 | Norris et al. |
| 2002/0026122 A1 | 2/2002 | Lee et al. |
| 2002/0026223 A1 | 2/2002 | Riff et al. |
| 2002/0035337 A1 | 3/2002 | Oka |
| 2002/0042632 A1 | 4/2002 | Iaizzo et al. |
| 2002/0072684 A1 | 6/2002 | Stearns |
| 2002/0072777 A1 | 6/2002 | Lu |
| 2002/0082645 A1 | 6/2002 | Sweeney |
| 2002/0091415 A1 | 7/2002 | Lovett et al. |
| 2002/0107450 A1 | 8/2002 | Ogura |
| 2002/0120298 A1 | 8/2002 | Kramer et al. |
| 2002/0123672 A1 | 9/2002 | Christophersom et al. |
| 2002/0123772 A1 | 9/2002 | Sun et al. |
| 2002/0128563 A1 | 9/2002 | Carlson et al. |
| 2002/0143262 A1 | 10/2002 | Bardy |
| 2002/0143369 A1 | 10/2002 | Hill et al. |
| 2002/0147401 A1 | 10/2002 | Oka |
| 2002/0151812 A1 | 10/2002 | Scheiner et al. |
| 2002/0151938 A1 | 10/2002 | Corbucci |
| 2003/0004549 A1 | 1/2003 | Hill et al. |
| 2003/0013974 A1 | 1/2003 | Natarajan et al. |
| 2003/0014083 A1 | 1/2003 | Kupper |
| 2003/0040676 A1 | 2/2003 | Prentice et al. |
| 2003/0045805 A1 | 3/2003 | Sheldon et al. |
| 2003/0045908 A1 | 3/2003 | Condie et al. |
| 2003/0055352 A1 | 3/2003 | Hayek et al. |
| 2003/0055461 A1 | 3/2003 | Girouard et al. |
| 2003/0060854 A1 | 3/2003 | Zhu |
| 2003/0069608 A1 | 4/2003 | Sweeney |
| 2003/0072458 A1 | 4/2003 | Halleck et al. |
| 2003/0078624 A1 | 4/2003 | Carlson et al. |
| 2003/0093002 A1 | 5/2003 | Kuo |
| 2003/0093003 A1 | 5/2003 | Watrous et al. |
| 2003/0105496 A1 | 6/2003 | Yu et al. |
| 2003/0105497 A1 | 6/2003 | Zhu et al. |
| 2003/0120159 A1 | 6/2003 | Mohler |
| 2003/0125774 A1 | 7/2003 | Salo |
| 2003/0139778 A1 | 7/2003 | Fischell et al. |
| 2003/0144702 A1 | 7/2003 | Yu et al. |
| 2003/0144703 A1 | 7/2003 | Yu et al. |
| 2003/0158492 A1 | 8/2003 | Sheldon et al. |
| 2003/0158584 A1 | 8/2003 | Cates et al. |
| 2003/0171791 A1 | 9/2003 | KenKnight et al. |
| 2003/0176896 A1 | 9/2003 | Lincoln et al. |
| 2003/0191503 A1 | 10/2003 | Zhu et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2003/0233130 A1 | 12/2003 | Padmanabhan et al. |
| 2003/0233132 A1 | 12/2003 | Pastore et al. |
| 2004/0015081 A1 | 1/2004 | Kramer et al. |
| 2004/0024423 A1 | 2/2004 | Lincoln et al. |
| 2004/0039295 A1 | 2/2004 | Olbrich et al. |
| 2004/0039419 A1 | 2/2004 | Stickney et al. |
| 2004/0039420 A1 | 2/2004 | Jayne et al. |
| 2004/0059238 A1 | 3/2004 | Fischell et al. |
| 2004/0064056 A1 | 4/2004 | Ogura |
| 2004/0073093 A1 | 4/2004 | Hatlestad |
| 2004/0078059 A1 | 4/2004 | Ding et al. |
| 2004/0078060 A1 | 4/2004 | Ding et al. |
| 2004/0088017 A1 | 5/2004 | Sharma et al. |
| 2004/0102712 A1 | 5/2004 | Belalcazar et al. |
| 2004/0102815 A1 | 5/2004 | Balczewski et al. |
| 2004/0106960 A1 | 6/2004 | Siejko et al. |
| 2004/0106961 A1 | 6/2004 | Siejko et al. |
| 2004/0106962 A1 | 6/2004 | Mai et al. |
| 2004/0111040 A1 | 6/2004 | Ni et al. |
| 2004/0116820 A1 | 6/2004 | Daum et al. |
| 2004/0116972 A1 | 6/2004 | Marcovecchio |
| 2004/0122484 A1 | 6/2004 | Hatlestad et al. |
| 2004/0127792 A1 | 7/2004 | Siejko et al. |
| 2004/0133247 A1 | 7/2004 | Stahmann et al. |
| 2004/0138572 A1 | 7/2004 | Thiagarajan |
| 2004/0167417 A1 | 8/2004 | Schulhauser et al. |
| 2004/0176810 A1 | 9/2004 | Stadler et al. |
| 2004/0215264 A1 | 10/2004 | Van Bentem |
| 2004/0215265 A1 | 10/2004 | Keizer |
| 2004/0220637 A1 | 11/2004 | Zdeblick et al. |
| 2004/0225332 A1 | 11/2004 | Gebhardt et al. |
| 2004/0230240 A1 | 11/2004 | Sun et al. |
| 2004/0230243 A1 | 11/2004 | Haefner et al. |
| 2004/0236239 A1 | 11/2004 | Murray et al. |
| 2004/0243192 A1 | 12/2004 | Hepp et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0004476 A1 | 1/2005 | Payvar et al. |
| 2005/0004485 A1 | 1/2005 | Crosby et al. |
| 2005/0027323 A1 | 2/2005 | Mulligan et al. |
| 2005/0033190 A1 | 2/2005 | Bauer |
| 2005/0038345 A1 | 2/2005 | Gorgenberg et al. |
| 2005/0043675 A1 | 2/2005 | Pastore et al. |
| 2005/0049492 A1 | 3/2005 | Sweeney et al. |
| 2005/0060001 A1 | 3/2005 | Singhal et al. |
| 2005/0065448 A1 | 3/2005 | Stahmann et al. |
| 2005/0065556 A1 | 3/2005 | Reghabi et al. |
| 2005/0075673 A1 | 4/2005 | Warkentin et al. |
| 2005/0090870 A1 | 4/2005 | Hine et al. |
| 2005/0096706 A1 | 5/2005 | Salo |
| 2005/0102001 A1 | 5/2005 | Maile et al. |
| 2005/0102002 A1 | 5/2005 | Salo et al. |
| 2005/0137483 A1 | 6/2005 | Fischell et al. |
| 2005/0137631 A1 | 6/2005 | Yu et al. |
| 2005/0143779 A1 | 6/2005 | Libbus |
| 2005/0148896 A1 | 7/2005 | Siejko et al. |
| 2005/0148897 A1 | 7/2005 | Cho et al. |
| 2005/0149129 A1 | 7/2005 | Libbus et al. |
| 2005/0149136 A1 | 7/2005 | Siejko et al. |
| 2005/0159781 A1 | 7/2005 | Hsu et al. |
| 2005/0197674 A1 | 9/2005 | McCabe et al. |
| 2005/0203579 A1 | 9/2005 | Sowelam et al. |
| 2005/0256542 A1 | 11/2005 | Pastore et al. |
| 2005/0261741 A1 | 11/2005 | Libbus et al. |
| 2005/0283195 A1 | 12/2005 | Pastore et al. |
| 2005/0288721 A1 | 12/2005 | Girouard et al. |

(56) References Cited

U.S. PATENT DOCUMENTS

| | | |
|---|---|---|
| 2006/0015148 A1 | 1/2006 | McCabe et al. |
| 2006/0020294 A1 | 1/2006 | Brockway et al. |
| 2006/0020295 A1 | 1/2006 | Brockway et al. |
| 2006/0025699 A1 | 2/2006 | Maile et al. |
| 2006/0030892 A1 | 2/2006 | Kadhiresan et al. |
| 2006/0041280 A1 | 2/2006 | Stahmann et al. |
| 2006/0047213 A1 | 3/2006 | Gavriely et al. |
| 2006/0106322 A1 | 5/2006 | Arand et al. |
| 2006/0110374 A1 | 5/2006 | Czeiger et al. |
| 2006/0116593 A1 | 6/2006 | Zhang et al. |
| 2006/0161070 A1 | 7/2006 | Siejko et al. |
| 2006/0167518 A1 | 7/2006 | Gill et al. |
| 2006/0206158 A1 | 9/2006 | Wu et al. |
| 2006/0247550 A1 | 11/2006 | Thiagarajan et al. |
| 2006/0247686 A1 | 11/2006 | Girouard et al. |
| 2006/0247700 A1 | 11/2006 | Jackson |
| 2006/0259087 A1 | 11/2006 | Baynham et al. |
| 2006/0259088 A1 | 11/2006 | Pastore et al. |
| 2006/0270939 A1 | 11/2006 | Wariar et al. |
| 2006/0282000 A1 | 12/2006 | Zhang et al. |
| 2006/0287684 A1 | 12/2006 | Baynham et al. |
| 2007/0043393 A1 | 2/2007 | Brockway et al. |
| 2007/0049835 A1 | 3/2007 | Goode |
| 2007/0054871 A1 | 3/2007 | Pastore et al. |
| 2007/0078491 A1 | 4/2007 | Siejko et al. |
| 2007/0123943 A1 | 5/2007 | Patangay et al. |
| 2007/0149890 A1 | 6/2007 | Li et al. |
| 2007/0150005 A1 | 6/2007 | Sih et al. |
| 2007/0150015 A1 | 6/2007 | Zhang et al. |
| 2007/0162080 A1 | 7/2007 | Brockway et al. |
| 2007/0162081 A1 | 7/2007 | Yu et al. |
| 2007/0179392 A1 | 8/2007 | Zhang |
| 2007/0191725 A1 | 8/2007 | Nelson |
| 2007/0239218 A1 | 10/2007 | Carlson et al. |
| 2007/0276453 A1 | 11/2007 | Hill et al. |
| 2007/0282380 A1 | 12/2007 | Brooke et al. |
| 2007/0299356 A1 | 12/2007 | Wariar et al. |
| 2008/0015652 A1 | 1/2008 | Maile et al. |
| 2008/0051672 A1 | 2/2008 | McCabe et al. |
| 2008/0058661 A1 | 3/2008 | Bardy |
| 2008/0058881 A1 | 3/2008 | Wagner et al. |
| 2008/0071315 A1 | 3/2008 | Baynham et al. |
| 2008/0081354 A1 | 4/2008 | Qu et al. |
| 2008/0082135 A1 | 4/2008 | Arcot et al. |
| 2008/0091138 A1 | 4/2008 | Pastore et al. |
| 2008/0103406 A1 | 5/2008 | Kameli |
| 2008/0119749 A1 | 5/2008 | Haro et al. |
| 2008/0119750 A1 | 5/2008 | Patangay et al. |
| 2008/0125820 A1 | 5/2008 | Stahmann et al. |
| 2008/0132972 A1 | 6/2008 | Shuros et al. |
| 2008/0140141 A1 | 6/2008 | Ben-David et al. |
| 2008/0177156 A1 | 7/2008 | Zhang et al. |
| 2008/0177191 A1 | 7/2008 | Patangay et al. |
| 2008/0177194 A1 | 7/2008 | Zhang et al. |
| 2008/0221636 A1 | 9/2008 | Pastore et al. |
| 2008/0228094 A1 | 9/2008 | Audet et al. |
| 2008/0262368 A1 | 10/2008 | Patangay et al. |
| 2009/0018461 A1 | 1/2009 | Siejko et al. |
| 2009/0025459 A1 | 1/2009 | Zhang et al. |
| 2009/0048641 A1 | 2/2009 | Libbus |
| 2009/0082781 A1 | 3/2009 | Tran et al. |
| 2009/0124916 A1 | 5/2009 | Sweeney et al. |
| 2009/0132000 A1 | 5/2009 | Brockway et al. |
| 2009/0143835 A1 | 6/2009 | Pastore et al. |
| 2009/0247889 A1 | 10/2009 | Maile et al. |
| 2009/0287106 A1 | 11/2009 | Zhang et al. |
| 2010/0099997 A1 | 4/2010 | Siejko et al. |
| 2010/0121391 A1 | 5/2010 | Brockway et al. |
| 2010/0249863 A1 | 9/2010 | Carlson et al. |
| 2011/0077543 A1 | 3/2011 | Patangay et al. |
| 2011/0077701 A1 | 3/2011 | Sih et al. |
| 2011/0077707 A1 | 3/2011 | Maile et al. |
| 2011/0098588 A1 | 4/2011 | Siejko et al. |
| 2011/0144709 A1 | 6/2011 | Baynham et al. |
| 2012/0271186 A1 | 10/2012 | Siejko et al. |
| 2013/0110189 A1 | 5/2013 | Baynham et al. |
| 2013/0296728 A1 | 11/2013 | Siejko et al. |

FOREIGN PATENT DOCUMENTS

| | | |
|---|---|---|
| EP | 0297675 A1 | 1/1989 |
| EP | 0467695 A2 | 1/1992 |
| EP | 0474958 A2 | 3/1992 |
| EP | 709058 A1 | 5/1996 |
| EP | 0709058 A1 | 5/1996 |
| EP | 0762908 B1 | 3/1997 |
| EP | 1179317 A2 | 2/2002 |
| EP | 1247485 A1 | 10/2002 |
| EP | 1904164 | 5/2011 |
| EP | 1838218 B1 | 7/2013 |
| JP | 63-290544 A | 11/1988 |
| JP | 03015441 | 1/1991 |
| JP | 4082538 | 3/1992 |
| JP | 06-277189 A | 10/1994 |
| JP | 7504597 A | 5/1995 |
| JP | 2000-060846 A | 2/2000 |
| JP | 2000-316825 | 11/2000 |
| JP | 2001145606 | 5/2001 |
| JP | 2004081854 | 3/2004 |
| JP | 2005501617 A | 1/2005 |
| JP | 2005063332 A | 3/2005 |
| JP | 2005177458 A1 | 7/2005 |
| JP | 2008539983 A | 11/2008 |
| JP | 4995191 A | 5/2012 |
| WO | WO-9400192 | 1/1994 |
| WO | WO-9725098 A1 | 7/1997 |
| WO | WO-9910042 A1 | 3/1999 |
| WO | WO-0007497 | 2/2000 |
| WO | WO-0108748 A1 | 2/2001 |
| WO | WO-0122885 A1 | 4/2001 |
| WO | WO-0124876 A1 | 4/2001 |
| WO | WO-0128625 | 4/2001 |
| WO | WO-0130436 A2 | 5/2001 |
| WO | WO-0156651 A1 | 8/2001 |
| WO | WO-0167948 A2 | 9/2001 |
| WO | WO-0176689 A2 | 10/2001 |
| WO | WO-02087694 A1 | 11/2002 |
| WO | WO-03041797 A2 | 5/2003 |
| WO | WO-2004012815 A1 | 2/2004 |
| WO | WO-2004035137 A1 | 4/2004 |
| WO | WO-2004050178 A1 | 6/2004 |
| WO | WO-2004060483 A1 | 7/2004 |
| WO | WO-2004066825 A2 | 8/2004 |
| WO | WO-2005074361 A2 | 8/2005 |
| WO | WO-2005122902 A1 | 12/2005 |
| WO | WO-2006028575 A2 | 3/2006 |
| WO | WO-2006028575 A3 | 3/2006 |
| WO | WO-2006041337 A1 | 4/2006 |
| WO | WO-2006078757 A1 | 7/2006 |
| WO | WO-2006121842 A2 | 11/2006 |
| WO | WO-2006124636 A2 | 11/2006 |
| WO | WO-2006124636 A3 | 11/2006 |
| WO | WO-2006127594 A2 | 11/2006 |
| WO | WO-2006127594 A3 | 11/2006 |
| WO | WO-2007126578 A2 | 11/2007 |
| WO | WO-2007126578 A3 | 11/2007 |
| WO | WO-2008063288 A2 | 5/2008 |
| WO | WO-2008063288 A3 | 5/2008 |
| WO | WO-2008130532 A1 | 10/2008 |

OTHER PUBLICATIONS

U.S. Appl. No. 10/138,046, Notice of Allowance mailed May 18, 2006, 6 pgs.

U.S. Appl. No. 10/138,046, Notice of allowance mailed Nov. 29, 2005, 5 pgs.

U.S. Appl. No. 10/138,046, Response filed Sep. 29, 2005 to Non Final Office Action mailed Jun. 29, 2005, 9 pgs.

U.S. Appl. No. 10/307,896, Notice of Allowance mailed May 30, 2006, 14 pgs.

U.S. Appl. No. 10/307,896, Notice of Allowance mailed Oct. 28, 2005, 14 pgs.

(56) References Cited

OTHER PUBLICATIONS

U.S. Appl. No. 10/334,694, Advisory Action mailed Dec. 18, 2007, 3 pgs.
U.S. Appl. No. 10/334,694, Advisory Action mailed Dec. 23, 2008, 3 pgs.
U.S. Appl. No. 10/334,694, Final Office Action mailed Oct. 1, 2007, 13 pgs.
U.S. Appl. No. 10/334,694, Final Office Action mailed Oct. 7, 2008, 14 pgs.
U.S. Appl. No. 10/334,694, Final Office Action mailed Nov. 27, 2009, 13 pgs.
U.S. Appl. No. 10/334,694, Non-Final Office Action mailed Mar. 18, 2009, 14 pgs.
U.S. Appl. No. 10/334,694, Non-Final Office Action mailed Mar. 19, 2008, 15 pgs.
U.S. Appl. No. 10/334,694, Non-Final Office Action mailed Apr. 20, 2007, 12 pgs.
U.S. Appl. No. 10/334,694, Non-Final Office Action mailed Apr. 30, 2010, 13 pgs.
U.S. Appl. No. 10/334,694, Non-Final Office Action mailed Nov. 27, 2006, 9 pgs.
U.S. Appl. No. 10/334,694, Notice of Allowance mailed Mar. 4, 2011, 7 pgs.
U.S. Appl. No. 10/334,694, Notice of Allowance mailed Oct. 5, 2010, 6 pgs.
U.S. Appl. No. 10/334,694, Response filed Feb. 27, 2007 to Non-Final Office Action mailed Nov. 27, 2006, 20 pgs.
U.S. Appl. No. 10/334,694, Response filed Mar. 1, 2010 to Final Office Action mailed Nov. 27, 2009, 21 pgs.
U.S. Appl. No. 10/334,694, Response filed Jun. 19, 2008 to Non-Final Office Action mailed Mar. 19, 2008, 20 pgs.
U.S. Appl. No. 10/334,694, Response filed Jul. 17, 2009 to Non Final Office Action mailed Mar. 18, 2009, 18 pgs.
U.S. Appl. No. 10/334,694, Response filed Jul. 27, 2010 to Non Final Office Action mailed Apr. 30, 2010, 19 pgs.
U.S. Appl. No. 10/334,694, Response filed Dec. 3, 2007 to Final Office Action mailed Oct. 1, 2007, 21 pgs.
U.S. Appl. No. 10/334,694, Response filed Dec. 8, 2008 to Final Office Action mailed Oct. 7, 2008, 18 pgs.
U.S. Appl. No. 10/703,175, Final Office Action mailed Oct. 12, 2006, 9 pgs.
U.S. Appl. No. 10/703,175, Non-Final Office Action mailed May 10, 2006, 7 pgs.
U.S. Appl. No. 10/703,175, Notice of Allowance mailed Mar. 19, 2007, 5 pgs.
U.S. Appl. No. 10/703,175, Response filed Aug. 9, 2006 to Non-Final Office Action mailed May 10, 2006, 20 pgs.
U.S. Appl. No. 10/703,175, Response filed Dec. 12, 2006 to Final Office Action mailed Oct. 12, 2006, 21 pgs.
U.S. Appl. No. 10/744,900, Non-Final Office Action mailed Jun. 21, 2006, 15 pgs.
U.S. Appl. No. 10/744,900, Notice of Allowance mailed Dec. 18, 2006, 5 pgs.
U.S. Appl. No. 10/744,900, Response filed Oct. 23, 2006 to Non Final Office Action mailed Jun. 21, 2006, 19 pgs.
U.S. Appl. No. 10/746,853, Final Office Action mailed May 22, 2007, 11 pgs.
U.S. Appl. No. 10/746,853, Non-Final Office Action mailed Sep. 26, 2007, 8 pgs.
U.S. Appl. No. 10/746,853, Non-Final Office Action mailed Dec. 19, 2006, 10 pgs.
U.S. Appl. No. 10/746,853, Notice of Allowance mailed May 30, 2008, 4 pgs.
U.S. Appl. No. 10/746,853, Response filed Jan. 17, 2008 to Non-Final Office Action mailed Sep. 26, 2007, 18 pgs.
U.S. Appl. No. 10/746,853, Response filed Mar. 15, 2007 to Non-Final Office Action mailed Dec. 19, 2006, 16 pgs.
U.S. Appl. No. 10/746,853, Response filed Jul. 23, 2007 to Final Office Action mailed May 22, 2007, 16 pgs.
U.S. Appl. No. 10/746,874, Response filed Apr. 17, 2006 to Restriction Requirement mailed Mar. 31, 2006, 14 pgs.
U.S. Appl. No. 10/746,874, Restriction Requirement mailed Mar. 31, 2006, 6 pgs.
U.S. Appl. No. 10/865,498, Non-Final Office Action mailed Sep. 11, 2006, 11 pgs.
U.S. Appl. No. 10/865,498, Notice of Allowance mailed Dec. 6, 2006, 12 pgs.
U.S. Appl. No. 10/865,498, Response filed Oct. 24, 2006 to Non Final Office Action mailed Sep. 11, 2006, 19 pgs.
U.S. Appl. No. 10/897,856, Advisory Action mailed Jun. 17, 2008, 3 pgs.
U.S. Appl. No. 10/897,856, Final Office Action mailed Jan. 4, 2008, 15 pgs.
U.S. Appl. No. 10/897,856, Non Final Office Action mailed Oct. 4, 2006, 15 pgs.
U.S. Appl. No. 10/897,856, Notice of Allowance mailed Sep. 15, 2008, 6 pgs.
U.S. Appl. No. 10/897,856, Response filed Jan. 2, 2007 to Non Final Office Action mailed Oct. 4, 2006, 24 pgs.
U.S. Appl. No. 10/897,856, Response filed Mar. 4, 2008 to Final Office Action mailed Jan. 4, 2008, 24 pgs.
U.S. Appl. No. 10/897,856, Supplemental Notice of Allowability mailed Oct. 22, 2008, 3 pgs.
U.S. Appl. No. 10/897,856, Supplemental Notice of Allowability mailed Dec. 3, 2008, 3 pgs.
U.S. Appl. No. 10/900,570, Non-Final Office Action mailed Jan. 10, 2008, 4 pgs.
U.S. Appl. No. 10/900,570, Non-Final Office Action mailed Jul. 25, 2008, 5 pgs.
U.S. Appl. No. 10/900,570, Notice of Allowance mailed Mar. 6, 2009, 6 pgs.
U.S. Appl. No. 10/900,570, Response filed Apr. 10, 2008 to Non-Final Office Action mailed Jan. 10, 2008, 7 pgs.
U.S. Appl. No. 10/900,570, Response filed Oct. 22, 2007 to Restriction Requirement mailed Sep. 27, 2007, 7 pgs.
U.S. Appl. No. 10/900,570, Response filed Nov. 25, 2008 to Non Final Office Action mailed Jul. 25, 2008, 9 pgs.
U.S. Appl. No. 10/900,570, Restriction Requirement mailed Sep. 27, 2007, 6 pgs.
U.S. Appl. No. 11/037,275, Examiner Interview Summary mailed Apr. 20, 2009, 2 pgs.
U.S. Appl. No. 11/037,275, Examiner Interview Summary mailed Sep. 5, 2008, 2 pgs.
U.S. Appl. No. 11/037,275, Final Office Action mailed Jun. 17, 2008, 12 pgs.
U.S. Appl. No. 11/037,275, Final Office Action mailed Jun. 17, 2009, 11 pgs.
U.S. Appl. No. 11/037,275, Non-Final Office Action mailed Jan. 15, 2009, 9 pgs.
U.S. Appl. No. 11/037,275, Non-Final Office Action mailed Dec. 12, 2007, 17 pgs.
U.S. Appl. No. 11/037,275, Notice of Allowance mailed Sep. 23, 2009, 6 pgs.
U.S. Appl. No. 11/037,275, Response filed Mar. 12, 2008 to Non Final Office Action mailed Dec. 12, 2007, 16 pgs.
U.S. Appl. No. 11/037,275, Response filed Apr. 15, 2009 to Non Final Office Action mailed Jan. 15, 2009, 12 pgs.
U.S. Appl. No. 11/037,275, Response filed Aug. 13, 2009 to Final Office Action mailed Jun. 17, 2009, 14 pgs.
U.S. Appl. No. 11/037,275, Response filed Sep. 17, 2008 to Final Office Action mailed Jun. 17, 2008, 12 pgs.
U.S. Appl. No. 11/129,050, Advisory Action mailed Jul. 28, 2008, 3 pgs.
U.S. Appl. No. 11/129,050, Final Office Action mailed May 12, 2008, 8 pgs.
U.S. Appl. No. 11/129,050, Non-Final Office Action mailed Nov. 26, 2007, 7 pgs.
U.S. Appl. No. 11/129,050, Notice of Allowance mailed Nov. 1, 2010, 6 pgs.
U.S. Appl. No. 11/129,050, Response filed Feb. 26, 2008 to Non-Final Office Action mailed Nov. 26, 2007, 14 pgs.

(56) References Cited

OTHER PUBLICATIONS

U.S. Appl. No. 11/129,050, Response filed Jul. 14, 2008 to Final Office Action mailed May 12, 2008, 13 pgs.
U.S. Appl. No. 11/129,050, Response filed Sep. 28, 2007 to Restriction Requirement mailed Aug. 1, 2007, 11 pgs.
U.S. Appl. No. 11/129,050, Supplemental Response filed Sep. 12, 2008 to Final Office Action mailed May 12, 2008, 12 pgs.
U.S. Appl. No. 11/135,985, Non-Final Office Action mailed Sep. 25, 2007, 11 pgs.
U.S. Appl. No. 11/135,985, Notice of Allowance mailed Apr. 25, 2008, 4 pgs.
U.S. Appl. No. 11/148,107, Examiner Interview Summary mailed Oct. 9, 2008, 4 pgs.
U.S. Appl. No. 11/148,107, Final Office Action mailed Jan. 14, 2009, 9 pgs.
U.S. Appl. No. 11/148,107, Non-Final Office Action mailed Jul. 18, 2008, 7 pgs.
U.S. Appl. No. 11/148,107, Non-Final Office Action mailed Jul. 18, 2008, 8 pgs.
U.S. Appl. No. 11/148,107, Notice of Allowance mailed Feb. 1, 2010, 4 pgs.
U.S. Appl. No. 11/148,107, Notice of Allowance mailed Mar. 30, 2009, 4 pgs.
U.S. Appl. No. 11/148,107, Notice of Allowance mailed Aug. 24, 2009, 4 pgs.
U.S. Appl. No. 11/148,107, Notice of Allowance mailed Aug. 30, 2010, 8 pgs.
U.S. Appl. No. 11/148,107, Notice of Allowance mailed Nov. 23, 2010, 6 pgs.
U.S. Appl. No. 11/148,107, Response filed Mar. 16, 2009 to Final Office Action mailed Jan. 14, 2009, 9 pgs.
U.S. Appl. No. 11/148,107, Response filed Jun. 30, 2008 to Restriction Requirement mailed May 30, 2008, 7 pgs.
U.S. Appl. No. 11/148,107, Response filed Oct. 20, 2008 to Non-Final Office Action mailed Jul. 18, 2008, 9 pgs.
U.S. Appl. No. 11/207,251, Final Office Action mailed Feb. 3, 2009, 9 pgs.
U.S. Appl. No. 11/207,251, Non-Final Office Action mailed Jun. 27, 2008, 8 pgs.
U.S. Appl. No. 11/207,251, Notice of Allowance mailed May 28, 2009, 4 pgs.
U.S. Appl. No. 11/207,251, Response filed Apr. 7, 2009 to Final Office Action mailed Feb. 3, 2009, 11 pgs.
U.S. Appl. No. 11/207,251, Response filed Sep. 29, 2008 to Non Final Office Action mailed Jun. 27, 2008, 14 pgs.
U.S. Appl. No. 11/275,800, Examiner Interview Summary mailed Aug. 8, 2008, 5 pgs.
U.S. Appl. No. 11/275,800, Final Office Action mailed Dec. 11, 2008, 10 pgs.
U.S. Appl. No. 11/275,800, Non-Final Office Action mailed May 2, 2008, 12 pgs.
U.S. Appl. No. 11/275,800, Response filed Feb. 11, 2009 to Non Final Office Action mailed Dec. 11, 2008, 14 pgs.
U.S. Appl. No. 11/275,800, Response filed Aug. 29, 2008 to Non-Final Office Action mailed May 2, 2008, 13 pgs.
U.S. Appl. No. 11/277,773, Non-Final Office Action mailed Jun. 25, 2008, 16 pgs.
U.S. Appl. No. 11/277,773, Examiner Interview Summary mailed Oct. 2, 2008, 2 pgs.
U.S. Appl. No. 11/277,773, Final Office Action mailed Jan. 28, 2009, 16 pgs.
U.S. Appl. No. 11/277,773, Non-Final Office Action mailed Apr. 21, 2009, 12 pgs.
U.S. Appl. No. 11/277,773, Non-Final Office Action mailed Oct. 8, 2009, 9 pgs.
U.S. Appl. No. 11/277,773, Notice of Allowance mailed Mar. 24, 2010, 6 pgs.
U.S. Appl. No. 11/277,773, Response filed Jan. 8, 2010 to Non Final Office Action mailed Oct. 8, 2009, 8 pgs.
U.S. Appl. No. 11/277,773, Response filed Mar. 30, 2009 to Final Office Action mailed Jan. 28, 2009, 14 pgs.
U.S. Appl. No. 11/277,773, Response filed Jun. 2, 2008 to Restriction Requirement mailed May 2, 2008, 26 pgs.
U.S. Appl. No. 11/277,773, Response filed Jul. 21, 2009 to Non Final Office Action mailed Apr. 21, 2009, 9 pgs.
U.S. Appl. No. 11/277,773, Response filed Oct. 27, 2008 to Non-Final Office Action mailed Jun. 25, 2008, 15 pgs.
U.S. Appl. No. 11/277,773, Restriction Requirement mailed May 2, 2008, 6 pgs.
U.S. Appl. No. 11/287,978, Examiner Interview Summary mailed Jan. 25, 2010, 3 pgs.
U.S. Appl. No. 11/287,978, Final Office Action mailed Jul. 21, 2010, 6 pgs.
U.S. Appl. No. 11/287,978, Non-Final Office Action mailed Jun. 26, 2009, 7 pgs.
U.S. Appl. No. 11/287,978, Response filed Sep. 16, 2010 to Final Office Action mailed Jul. 21, 2010, 15 pgs.
U.S. Appl. No. 11/287,978, Response filed Sep. 28, 2009 to Non Final Office Action mailed Jun. 26, 2009, 10 pgs.
U.S. Appl. No. 11/382,849, Final Office Action mailed Jan. 28, 2010, 7 pgs.
U.S. Appl. No. 11/382,849, Non-Final Office Action mailed May 12, 2010, 5 pgs.
U.S. Appl. No. 11/382,849, Non-Final Office Action mailed Aug. 31, 2009, 8 pgs.
U.S. Appl. No. 11/382,849, Notice of Allowance mailed Oct. 15, 2010, 6 pgs.
U.S. Appl. No. 11/382,849, Response filed Apr. 26, 2010 to Final Office Action mailed Jan. 28, 2010, 10 pgs.
U.S. Appl. No. 11/382,849, Response filed Jun. 8, 2009 to Restriction Requirement mailed May 6, 2009, 8 pgs.
U.S. Appl. No. 11/382,849, Response filed Aug. 2, 2010 to Non Final Office Action mailed May 12, 2010, 7 pgs.
U.S. Appl. No. 11/382,849, Response filed Nov. 30, 2009 to Non Final Office Action mailed Aug. 31, 2009, 11 pgs.
U.S. Appl. No. 11/382,849, Restriction Requirement mailed May 6, 2009, 6 pgs.
U.S. Appl. No. 11/426,835, Final Office Action mailed Nov. 12, 2010, 13 pgs.
U.S. Appl. No. 11/426,835, Non-Final Office Action mailed Apr. 1, 2010, 13 pgs.
U.S. Appl. No. 11/426,835, Response filed Feb. 14, 2011 to Final Office Action mailed Nov. 12, 2010, 15 pgs.
U.S. Appl. No. 11/426,835, Response filed Aug. 2, 2010 to Non Final Office Action mailed Apr. 1, 2010, 16 pgs.
U.S. Appl. No. 11/426,835, Response filed Nov. 6, 2009 to Restriction Requirement mailed Oct. 6, 2009, 12 pgs.
U.S. Appl. No. 11/426,835, Restriction Requirement mailed Oct. 6, 2009, 9 pgs.
U.S. Appl. No. 11/465,878, Notice of Allowance mailed Oct. 8, 2009, 8 pgs.
U.S. Appl. No. 11/625,003, Examiner Interview Summary mailed Nov. 4, 2009, 4 pgs.
U.S. Appl. No. 11/625,003, Non Final Office Action mailed Jul. 10, 2009, 12 pgs.
U.S. Appl. No. 11/625,003, Notice of Allowance mailed Feb. 1, 2010, 6 pgs.
U.S. Appl. No. 11/625,003, Response filed Apr. 30, 2009 to Restriction Requirement mailed Mar. 31, 2009, 12 pgs.
U.S. Appl. No. 11/625,003, Response filed Nov. 2, 2009 to Non Final Office Action mailed Jul. 10, 2009, 17 pgs.
U.S. Appl. No. 11/625,003, Restriction Requirement mailed Mar. 31, 2009, 6 pgs.
U.S. Appl. No. 11/778,527, Non-Final Office Action mailed Feb. 23, 2010, 4 pgs.
U.S. Appl. No. 11/778,527, Non-Final Office Action mailed Aug. 24, 2009, 7 pgs.
U.S. Appl. No. 11/778,527, Notice of Allowance mailed Jul. 29, 2010, 4 pgs.
U.S. Appl. No. 11/778,527, Response filed May 19, 2010 to Non Final Office Action mailed Feb. 23, 2010, 7 pgs.

(56) References Cited

OTHER PUBLICATIONS

U.S. Appl. No. 11/778,527, Response filed Nov. 24, 2009 to Non Final Office Action mailed Aug. 24, 2009, 11 pgs.
U.S. Appl. No. 12/510,962, Non-Final Office Action mailed Dec. 28, 2010, 9 pgs.
U.S. Appl. No. 12/510,962, Notice of Allowance mailed Jun. 8, 2011, 5 pgs.
U.S. Appl. No. 12/510,962, Response filed Mar. 28, 2011 to Non-Final Office Action mailed Dec. 28, 2011, 10 pgs.
U.S. Appl. No. 12/645,906, Notice of Allowance mailed Jan. 26, 2011, 8 pgs.
U.S. Appl. No. 12/813,073, Non-Final Office Action mailed Sep. 3, 2010, 7 pgs.
U.S. Appl. No. 12/813,073, Notice of Allowance mailed Dec. 29, 2010, 6 pgs.
U.S. Appl. No. 12/813,073, Response filed Nov. 29, 2010 to Non Final Office Action mailed Sep. 3, 2010, 9 pgs.
European Application Serial No. 03800278.8, Communication dated Oct. 17, 2007, 4 pgs.
European Application Serial No. 03800278.8, Response filed Feb. 18, 2008 to Communication dated Oct. 17, 2007, 14 pgs.
European Application Serial No. 05806944.4, Office Action mailed Apr. 14, 2008, 8 pgs.
European Application Serial No. 05806944.4, Response filed Oct. 17, 2008 to Office Action mailed Apr. 14, 2008, 22 pgs.
European Application Serial No. 06718817.7, Communication dated Nov. 15, 2007, 2 pgs.
European Application Serial No. 06718817.7, Office Action mailed Apr. 9, 2010, 4 pgs.
European Application Serial No. 06718817.7, Response filed Mar. 25, 2008 to Communication dated Nov. 15, 2007, 16 pgs.
European Application Serial No. 06718817.7, Response filed Aug. 19, 2010 to Office Action mailed Apr. 9, 2010, 11 pgs.
European Application Serial No. 06752527.9, Communication mailed Mar. 8, 2010, 6 pgs.
European Application Serial No. 06770836.2, Office Action mailed—May 20, 2009, 3 pgs.
European Application Serial No. 07753005.3, Communication dated Nov. 5, 2008, 2 pgs.
European Application Serial No. 07753005.3, Response filed Dec. 2, 2008 to Communication dated Nov. 5, 2008, 9 pgs.
European Application Serial No. 07797336.0, Communication mailed Mar. 10, 2010, 3 pgs.
European Application Serial No. 07797336.0, Response filed Jul. 6, 2009 to Communication mailed Feb. 24, 2009, 20 pgs.
European Application Serial No. 07797336.0, Response filed Jul. 7, 2010 to Office Action dated Mar. 10, 2010, 5 pgs.
International Application Serial No. PCT/US2006/001801, International Search Report and Written Opinion mailed Jun. 16, 2006, 12 pgs.
International Application Serial No. PCT/US2007/006345, International Search Report mailed Oct. 24, 2007, 6 pgs.
International Application Serial No. PCT/US2007/006345, Written Opinion mailed Oct. 24, 2007, 8 pgs.
International Application Serial No. PCT/US2007/021503, International Search Report mailed Jun. 5, 2008, 4 pgs.
International Application Serial No. PCT/US2007/021503, Written Opinion mailed Jun. 5, 2008, 7 pgs.
International Application Serial No. PCT/US2007/068217, International Search Report mailed Oct. 30, 2007, 5 pgs.
International Application Serial No. PCT/US2007/068217, Written Opinion mailed Oct. 30, 2007, 8 pgs.
International Application Serial No. PCT/US2008/004832, International Search Report mailed Sep. 3, 2008, 6 pgs.
International Application Serial No. PCT/US2008/004832, Written Opinion mailed Sep. 3, 2008, 7 pgs.
Japanese Application Serial No. 2004-565783, Amendment and Argument filed Feb. 5, 2010 to Office Action Mailed Nov. 11, 2009, (w/ English Translation of Amended Claims), 14 pgs.
Japanese Application Serial No. 2004-565783, Office Action mailed Mar. 11, 2010, (w/ English Translation), 4 pgs.
Japanese application Serial No. 2004-565783, Office Action mailed Nov. 11, 2009, (w/ English Translation), 4 pgs.
Japanese Application Serial No. 2008-511421, Voluntary Amendment filed Apr. 27, 2009, (w/ English Translation of Amended Claims), 11 pgs.
Japanese Application Serial No. 2009-502827, Amended Claims filed Mar. 4, 2010, (w/ English Translation), 15 pgs.
Aaron, S. D, et al., "How accurate is spirometry at predicting restrictive pulmonary impairment?", Chest, 115(3), XP002362629 ISSN: 0012-3692, (Mar. 1999), 869-873.
Abrams, Jonathan, "Current Concepts of the Genesis of Heart Sounds", JAMA 239(26), (Jun. 30, 1978).
Adolph, R. J., et al., "The clinical value of frequency analysis of the first heart sound in myocardial infarction.", Circulation, 41(6), (Jun. 1970), 1003-14.
Amende, I., "Hemodynamics in ischemia: diastolic phase", Z. Kardiol., 73 Suppl 2, [Article in German With English Abstract], (1984), 127-33.
Auricchio, A., et al., "Cardiac Resynchronization Therapy Restores Optimal Atrioventricular Mechanical Timing in Heart Failure Patients with Ventricular Conduction Delay", Journal of the American College of Cardiology, 39(7), (2002), 1163-1169.
Baynham, Tamara C, "Method and Apparatus for Cardiac Protection Pacing", U.S. Appl. No. 11/129,050, filed May 13, 2005, 33 pgs.
Breithardt, O A, et al., "Acute effects of cardiac resynchronization therapy on functional mitral regurgitation in advanced systolic heart failure", Journal of the American College of Cardiology, 41(5), (May 21, 2003), 765-70.
Brockway, Marina, et al., "Method and Apparatus for Monitoring Heart Failure Patients With Cardiopulmonary Comorbidities", U.S. Appl. No. 10/897,856, filed Jul. 23, 2004, 54 pgs.
Brockway, Marina, et al., "Method and Apparatus for Optimization of Cardiac Resynchronization Therapy Using Heart Sounds", U.S. Appl. No. 10/865,498, filed Jun. 10, 2004, 45 pgs.
Carabello, B A, "Mitral valve disease", Current Problems in Cardiology,18(7), (Jul. 1993), 423-78.
Carlson, Gerrard M, et al., "Hemodynamic Stability Assessment Based on Heart Sounds", U.S. Appl. No. 11/277,773, filed Mar. 29, 2006, 39 pgs.
Carlson, Gerrard M, et al., "Managing Preload Reserve by Tracking the Ventricular Operating Point With Heart Sounds", U.S. Appl. No. 11/189,462, filed Jul. 26, 2005, 36 pgs.
Clarke, W. B., et al., "Spectral energy of the first heart sound in acute myocardial ischemia. A correlation with electrocardiographic, hemodynamic, and wall motion abnormalities.", Circulation, 57(3), (Mar. 1978), 593-8.
Collins, Sean, "Diagnostic Utility of an S3 in Dyspneic ED Patients", Inovise Medical Inc, University of Cincinnati Medical Center, (2005), 6 Pages.
Ding, Jiang, et al., "Cardiac Pacing Using Adjustable Atrio-Ventricular Delays", U.S. Appl. No. 10/008,830, filed Dec. 7, 2001, 1-42.
Ding, Jiang, et al., "Cardiac Pacing Using Adjustable Atrio-Ventricular Delays", U.S. Appl. No. 10/243,811 mailed Sep. 13, 2002, 1-39.
Dreuw, P., et al., "Tracking Using Dynamic Programming for Appearance-Based Sign Language Recognition", Proceedings of the 7th International Conference on Automatic Face and Gesture Recognition, (2006), 293-298.
Dzwonczyk, R., et al., "Myocardial electrical impedance responds to ischemia and reperfusion in humans", IEEE Transactions on Biomedical Engineering, 51(12), (Dec. 2004), 2206-2209.
Fenster, M S, et al., "Mitral regurgitation: an overview", Curr Probl Cardiol., 20(4), (Apr. 1995), 193-280.
Hada, Yoshiyuki, et al., "Pulsus alternans determined by biventricular simultaneous systolic time intervals", Circulation, 65(3), (Mar. 1982), 617-26.
Haro, Carlos, et al., "Respiration-Synchronized Heart Sound Trending", U.S. Appl. No. 11/561,428, filed Nov. 20, 2006, 54 pgs.

(56) References Cited

OTHER PUBLICATIONS

Ji, J., "An Ultraminiature CMOS Pressure Sensor for a Multiplexed Cardiovascular Catheter", IEEE Transactions on Electron Devices, vol. 39, No. 10, (Oct. 1992), pp. 2260-2267.
Kameli, Nader, "Integrated System for Managing Patients With Heart Failure", U.S. Appl. No. 11/553,103, filed Oct. 26, 2006, 41 pgs.
Kinderman, Michael, et al., "Optimizing the AV Delay in DDD Pacemaker Patients with High Degree AV Block: Mitral Valve Doppler Versus Impedance Cardiography", PACE, vol. 20, (Oct. 1997), 2453-2462.
Kis, A., "Repeated cardiac pacing extends the time during which canine hearts are protected against ischaemia-induced arrhythmias : role of nitric oxide.", Journal of Molecular and Cellular Cardiology, 31(6), (Jun. 1999), 1229-1241.
Konta, Tsuyoshi, et al., "Significance of Discordant ST Alternans in Ventricular Fibrillation", Circulation, 82(6), (Dec. 1990), 2185-2189.
Krayenbuhl, H. P., "Hemodynamics in ischemia. Systolic phase", Z. Kardiol., 73 Suppl 2, [Article in German with English Abstract], (1984), 119-25.
Leatham, A, "Splitting of the First and Second Heart Sounds", Lancet, 267 (6839), (Sep. 25, 1954), 607-614.
Lee, Y. C, et al., "Pulsus alternans in patients with congestive cardiomyopathy", Circulation, 65(7), (Jun. 1982), 1533-4.
Leonelli, Fabio M, et al., "Systolic and Diastolic Effects of Variable Atroventricular Delay and Patients with Complete Hear Block and Normal Ventricular Function", Amer. J-Cardiology, vol. 80, (Aug. 1, 1997), 294-298.
Maile, Keith R., et al., "A Dual-Use Sensor for Rate Responsive Pacing and Heart Sound Monitoring", U.S. Appl. No. 10/703,175, filed Nov. 6, 2003, 41 pgs.
Maile, Keith R., et al., "Determining a Patient's Posture From Mechanical Vibrations of the Heart", U.S. Appl. No. 10/900,570, filed Jul. 28, 2004, 24 pgs.
Makhoul, John, "Linear Prediction: A Tutorial Review", Proceedings of the IEEE, 63, (Apr. 1975), 561-580.
Marcus, G. M., et al., "Association Between Phonocardiographic Third and Fourth Heart Sounds and Objective Measures of Left Ventricular Function", JAMA, 293(18), (May 11, 2005), 2238-44.
Min, Mart, "Electrical Impedance and Cardiac Monitoring-Technology, Potential and Applications", International Journal of Bioelectromagnetism, 5(1), (2003), 53-56.
Mower, Morton, , U.S. Patent Office search results for U.S. Appl. No. 10/214,474, filed Aug. 8, 2002, entitled "Method and Apparatus for Treating Hemodynamic Disfunction", 3 pgs.
Nesto, R. W., et al., "The ischemic cascade: temporal sequence of hemodynamic, electrocardiographic and symptomatic expressions of ischemia.", American Journal of Cardiology, 59(7), (Mar. 9, 1987), 23C-30C.
Obaidat, M. S, et al., "Performance of the Short-Time Fourier Transform and Wavelet Transform to Phonocardiogram Signal Analysis", Proceedings of the 1992 ACM/SIGAPP Symposium on Applied Computing ACM, Applied Computing: Technological Challenges of the 1990s, (1992), 856-862.
Obaidat, M. S., et al., "Performance of the short-time Fourier transform and wavelet transform to phonocardiogram signal analysis", Database Inspec [Online] The Institution of Electrical Engineers, Stevenage, GB, (1992).
Ostadal, Petr, et al., "The effect of early treatment by cerivastatin on the serum level of C-reactive protein, interleukin-6, and interleukin-8 in patients with unstable angina and non-Q-wave myocardial infarction", Molecular and Cellular Biochemistry, 246, (2003), 45-50.
Palomo, A R, et al., "Echo-phonocardiographics determination of left atrial and left ventrical filling pressures with and without mitral stenosis", Circulation, vol. 61, No. 5, (May 1980), 1043-1047.
Panju, Akbar A, et al., "Is This Patient Having a Myocardial Infarction?", JAMA, 280(14), (Oct. 14, 1998), 1256-1263.
Paolocci, Nazareno, et al., "Positive inotropic and lusitropic effects of HNO/NO—in failing hearts: Independence from beta-adrenergic signaling", Proceedings of the National Academy of Sciences USA, 100(9), (Apr. 29, 2003), 5537-5542.
Pastore, Joseph M, et al., "Method and Apparatus for Detecting Acoustic Oscillations in Cardiac Rythm", U.S. Appl. No. 10/138,046, filed May 3, 2002, 25 pgs.
Pastore, Joseph M, "Method and Apparatus for Detecting Oscillations in Cardiac Rhythm", U.S. Appl. No. 10/172,825, filed Jun. 14, 2002, 33 pgs.
Patangay, Ahilash, et al., "Ischemia Detection Using Heart Sound Timing", U.S. Appl. No. 11/625,003, filed Jan. 19, 2007, 69 pgs.
Pinchak, Alfred C, et al., "Multiaxial Accelerometers", Encyclopedia of Medical Devices and Instrumentation, vol. 1, Department of Electrical and Computer Engineering, (1988), 11 Pages.
Prinzen, Frits W, "Mapping of regional myocardial strain and work during ventricular pacing: experimental study using magnetic resonance imaging tagging", Journal of the American College of Cardiology, 33(6), (May 1999), 1735-1742.
Ritter, P., et al., "A Built-In System Based on the Peak Endocardial Acceleration (PEA) for AV-Delay Optimization in DDDR Pacing", PACE, 20(5) (Part II), (Abstract of Paper presented at EUROPACE '97), (May 1997), 1567.
Ritter, P., et al., "New Method for Determining the Optimal Atrio-Ventricular Delay in Patients Place in DDD Mode for Complete Atrio-Ventricular Block", NASPE Abstracts, (Abstract No. 237), (1995), p. 885.
Rosa, A., et al., "Ectopic Pacing at Physiological Rate Improves Postanoxic Recovery of the Developing Heart", Am. J. Physiol.-Heart Circ. Physiol., 284, (2003), H2384-H2392.
Rubenstein, Donald S, et al., "Premature Beats Elicit a Phase Reversal of Mechanoelectrical Alternans in Cat Ventricular Myocytes", Circulation, vol. 91, No. 1, Jan. 1995, American Heart Association, (Jan. 1, 1995), 201-214.
Sakamoto, T., et al., "Hemodynamic determinants of the amplitude of the first heart sound", Circulation Research, 16, (1965), 45-57.
Salerno, D. M., "Seismocardiography for monitoring changes in left ventricular function during ischemia.", Chest, 100(4), (Oct. 1991), 991-3.
Say, O, et al., "Classification of heart sounds by using wavelet transform", 24th Annual Conference and the Annual Fall Meeting of the Biomedical Engineering Society] EMBS/BMES Conference, vol. 1, (2002), 128-129.
Schaefer, Saul, et al., "Clinical and hemodynamic characteristics of patients with inducible pulsus alternans", American Heart Journal, vol. 115, No. 6, (Jun. 1988), 1251-7.
Sheiban, I., et al., "Time course and determinants of left ventricular function recovery after primary angioplasty in patients with acute myocardial infarction", J Am Coll Cardiol., 38(2), (Aug. 2001), 464-71.
Siejko, K. Z., et al., "Method for Correction of Posture Dependence on Heart Sounds", U.S. Appl. No. 11/037,275, filed Jan. 18, 2005, 26 pgs.
Siejko, Krzysztof Z, et al., "A Third Heart Sound Activity Index for Heart Failure Monitoring", U.S. Appl. No. 11/465,878, filed Aug. 21, 2006, 35 pgs.
Siejko, Krzysztof Z., "A Third Heart Sound Activity Index for Heart Failure Monitoring", U.S. Appl. No. 10/746,874, filed Dec. 24, 2003, 41 pgs.
Siejko, Krzysztof Z., et al., "Method and Apparatus for Third Heart Sound Detection", U.S. Appl. No. 10/746,853, filed Dec. 24, 2003, 40 pgs.
Siejko, Krzysztof Z, et al., "Physiological Event Detection Systems and Methods", U.S. Appl. No. 11/276,735, filed Mar. 13, 2006, 56 pgs.
Smith, Damon, et al., "Influence of the Aortic Component of the Second Heart Sound on Left Ventricular Maximal Negative dP/dt in the Dog", Am. J. Cardiol., 55: 205, (1985), 205-209.
Smith, R.A., et al., "An intranet database for pacemaker patients", International Journal of Medical Informatics, 47, (1997), 79-82.
Stahmann, Jeffrey, et al., "Thoracic Impedance Detection With Blood Resistivity Compensation", U.S. Appl. No. 10/921,503, filed Aug. 19, 2004, 38 pgs.
Stein, Emanuel, et al., "Rapid Interpretation of Heart Sounds and Murmurs", Baltimore : Williams & Wilkins, 4th ed., (1997), 85-105.

(56) References Cited

OTHER PUBLICATIONS

Tavel, Morton E, "The Appearance of Gallop Rhythm after Exercise Stress Testing", Clin. Cardiol., vol. 19, (1996), 887-891.

Theres, Heinz P, et al., "Detection of acute myocardial ischemia during percutaneous transluminal coronary angioplasty by endocardial acceleration.", Pacing Clin Electrophysiol., vol. 27, No. 5, (May 2004), 621-625.

Theroux, P., et al., "Regional Myocardial function in the conscious dog during acute coronary occlusion and responses to morphine, propranolol, nitroglycerin, and lidocaine.", Circulation, 53(2), (Feb. 1976), 302-14.

Wariar, R., et al., "Systems and Methods for Multi-Axis Cardiac Vibration Measurements", U.S. Appl. No. 11/135,985, filed May 24, 2004, 35 pgs.

Wariar, Ramesh, et al., "Detection of Myocardial Ischemia From the Time Sequence of Implanted Sensor Measurements", U.S. Appl. No. 11/426,835, filed Jun. 27, 2006, 41 pgs.

Watanabe, M., et al., "Developmental Remodeling and Shortening of Cardiac Outflow Tract Involves Myocyte Programmed Cell Death", Development, 125(19), (1998), 3809-3820.

Weissler, A. M., "Systolic time intervals in heart failure in man", Circulation, 37(2), (Feb. 1968), 149-59.

Wood, J. C, et al., "Time-Frequency Transforms: A New Approach to First Heart Sound Frequency Dynamics", IEEE Transactions on Biomedical Engineering, 39 (7), IEEE Service Center, US, (Jul. 1, 1992), 730-740.

Xu, J, et al., "A new, simple, and accurate method for non-invasive estimation of pulmonary arterial pressure", Heart 88, (2002), 76-80.

Yu, Yinghong, et al., "Method and Apparatus for Optimizing Stroke Volume During DDD Resynchronization Therapy Using Adjustable Atrio-Ventricular Delays", U.S. Appl. No. 10/314,899, filed Dec. 9, 2002, 1-50.

Yu, Yinghong, et al., "Method and Apparatus for Optimizing Ventricular Synchrony During DDD Resynchronization Therapy Using Adjustable Atrio-Ventricular Delays", U.S. Appl. No. 10/314,910, filed Dec. 9, 2002, 1-50.

Zanon, F, et al., "Reduced mitral regurgitation in heart failure patients submitted to cardiac resynchronization therapy: a short-term prospective study", Italian Heart Journal, 5(11), (Nov. 2004), 826-30.

Zhang, Y., et al., "Ischemia Detection Using a Heart Sound Sensor", U.S. Appl. No. 11/148,107, filed Jun. 8, 2005, 41 pgs.

Zhao, et al., "Inhibition of myocardial injury by ischemic postconditioning during reperfusion: comparison with ischemic preconditioning", Am J Physiol Heart Circ Physiol, 285(2), (Aug. 2003), H579-H588.

Zin, Z M, et al., "Wavelet analysis and classification of Mitral regurgitation and normal heart sounds based on artificial neural networks", Seventh International Symposium on Signal Processing and Its Applications, vol. 2, (Jul. 1-4, 2003), 619-620.

U.S. Appl. No. 10/334,694, Response filed Jul. 20, 2007 to Non-Final Office Action mailed Apr. 20, 2007, 18 pgs.

U.S. Appl. No. 10/746,874, Notice of Allowance mailed May 19, 2006, 9 pgs.

U.S. Appl. No. 10/865,498, Response filed Oct. 24, 2006 to Non-Final Office Action mailed Sep. 11, 2006, 19 pgs.

U.S. Appl. No. 11/113,828, Non-Final Office Action mailed Mar. 5, 2008, 8 pgs.

U.S. Appl. No. 11/129,050, Advisory Action mailed Jul. 14, 2009, 3 pgs.

U.S. Appl. No. 11/129,050, Examiner Interview Summary mailed Feb. 11, 2009, 2 pgs.

U.S. Appl. No. 11/129,050, Final Office Action mailed Apr. 21, 2009, 10 pgs.

U.S. Appl. No. 11/129,050, Non Final Office Action mailed Nov. 6, 2008, 7 pgs.

U.S. Appl. No. 11/129,050, Notice of Allowance mailed Apr. 1, 2010, 6 pgs.

U.S. Appl. No. 11/129,050, Notice of Allowance mailed Jul. 16, 2010, 4 pgs.

U.S. Appl. No. 11/129,050, Notice of Allowance mailed Aug. 24, 2009, 7 pgs.

U.S. Appl. No. 11/129,050, Notice of Allowance mailed Dec. 12, 2009, 4 pgs.

U.S. Appl. No. 11/129,050, Response filed Feb. 23, 2009 to Non Final Office Action mailed Nov. 6, 2008, 13 pgs.

U.S. Appl. No. 11/129,050, Response filed Jul. 22, 2009 to Final Office Action mailed Apr. 21, 2009, 9 pgs.

U.S. Appl. No. 11/129,050, Restriction Requirement mailed Aug. 1, 2007, 6 pgs.

U.S. Appl. No. 11/148,107, Restriction Requirement mailed May 30, 2008, 6 pgs.

U.S. Appl. No. 11/207,251, Notice of Allowance mailed Sep. 28, 2009, 4 pgs.

U.S. Appl. No. 11/287,978, Notice of Allowance mailed Sep. 19, 2011, 7 pgs.

U.S. Appl. No. 11/318,263, Final Office Action mailed Mar. 17, 2009, 11 pgs.

U.S. Appl. No. 11/318,263, Final Office Action mailed Jun. 3, 2010, 10 pgs.

U.S. Appl. No. 11/318,263, Non Final Office Action mailed Nov. 27, 2009, 8 pgs.

U.S. Appl. No. 11/318,263, Non-Final Office Action mailed Aug. 20, 2008, 9 pgs.

U.S. Appl. No. 11/318,263, Notice of Allowance mailed Sep. 29, 2010, 6 pgs.

U.S. Appl. No. 11/318,263, Response filed Feb. 26, 2010 to Non-Final Office Action mailed Nov. 27, 2009, 11 pgs.

U.S. Appl. No. 11/318,263, Response filed May 18, 2009 to Final Office Action mailed Mar. 17, 2009, 12 pgs.

U.S. Appl. No. 11/318,263, Response filed May 22, 2008 to Restriction Requirement mailed Apr. 23, 2008, 10 pgs.

U.S. Appl. No. 11/318,263, Response filed Aug. 2, 2010 to Final Office Action mailed Jun. 3, 2010, 13 pgs.

U.S. Appl. No. 11/318,263, Response filed Aug. 12, 2009 to Restriction Requirement mailed Jul. 14, 2009, 9 pgs.

U.S. Appl. No. 11/318,263, Response filed Nov. 20, 2008 to Non Final Office Action mailed Aug. 20, 2008, 12 pgs.

U.S. Appl. No. 11/318,263, Restriction Requirement mailed Apr. 23, 2008, 7 pgs.

U.S. Appl. No. 11/318,263, Restriction Requirement mailed Jul. 14, 2009, 5 pgs.

U.S. Appl. No. 11/465,878, Issue Notification mailed Jun. 15, 2012, 1 pg.

U.S. Appl. No. 11/465,878, Notice of Allowance mailed Mar. 5, 2012, 7 pgs.

U.S. Appl. No. 11/780,405, Non-Final Office Action mailed Apr. 12, 2010, 7 pgs.

U.S. Appl. No. 12/319,642, Notice of Allowance mailed Apr. 13, 2011, 5 pgs.

U.S. Appl. No. 12/319,642, Notice of Allowance mailed Jul. 19, 2011, 5 pgs.

U.S. Appl. No. 12/319,642, Response filed Mar. 21, 2011 to Non Final Office Action mailed Dec. 21, 2010, 14 pgs.

U.S. Appl. No. 12/955,065, Non Final Office Action mailed Dec. 30, 2013, 9 pgs.

U.S. Appl. No. 12/985,055, Non Final Office Action mailed Jun. 20, 2013, 6 pgs.

U.S. Appl. No. 12/985,055, Notice of Allowance mailed Sep. 27, 2013, 6 pgs.

U.S. Appl. No. 12/985,055, Response filed Sep. 12, 2013 to Non Final Office Action mailed Jun. 20, 2013, 8 pgs.

U.S. Appl. No. 13/019,888, Non Final Office Action mailed Jun. 29, 2012, 9 pgs.

U.S. Appl. No. 13/019,888, Notice of Allowance mailed Nov. 6, 2012, 8 pgs.

U.S. Appl. No. 13/019,888, Response filed May 2, 2012 to Restriction Requirement mailed Apr. 2, 2012, 8 pgs.

U.S. Appl. No. 13/019,888, Response filed Sep. 28, 2012 to Non Final Office Action mailed Jun. 29, 2012, 10 pgs.

U.S. Appl. No. 13/019,888, Restriction Requirement mailed Apr. 2, 2012, 5 pgs.

(56) References Cited

OTHER PUBLICATIONS

U.S. Appl. No. 13/029,631, Non Final Office Action mailed Apr. 12, 2012, 7 pgs.
U.S. Appl. No. 13/029,631, Notice of Allowance mailed Aug. 24, 2012, 7 pgs.
U.S. Appl. No. 13/029,631, Response filed Jul. 10, 2012 to Non Final Office Action mailed Apr. 12, 2012, 8 pgs.
U.S. Appl. No. 13/540,092, Response filed Mar. 19, 2013 to Non Final Office Action mailed Dec. 24, 2012, 7 pgs.
U.S. Appl. No. 13/540,092, Non Final Office Action mailed Dec. 24, 2012, 8 pgs.
U.S. Appl. No. 13/540,092, Notice of Allowance mailed Apr. 3, 2013, 6 pgs.
U.S. Appl. No. 13/721,796, Non Final Office Action mailed May 3, 2013, 7 pgs.
U.S. Appl. No. 13/721,796, Non Final Office Action mailed Oct. 23, 2013, 7 pgs.
U.S. Appl. No. 13/933,937, Response filed Dec. 11, 2013 to Non Final Office Action mailed Sep. 26, 2013, 9 pgs.
U.S. Appl. No. 13/933,937, Final Office Action mailed Jan. 15, 2014, 7 pgs.
U.S. Appl. No. 13/933,937, Non Final Office Action mailed Sep. 26, 2013, 9 pgs.
European Application Serial No. 06718817.7, Summons to Attend Oral Proceedings mailed Aug. 21, 2012, 10 pgs.
European Application Serial No. 06752527.9, Response filed Jul. 7, 2010 to Office Action dated Mar. 8, 2010, 15 pgs.
European Application Serial No. 06752527.9, Summons to Attend Oral Proceedings Received mailed Jul. 23, 2010, 3 pgs.
European Application Serial No. 06762527.9, Communication pursuant to Rules 161 to 182 EPC mailed Mar. 3, 2008, 2 pgs.
European Application Serial No. 06762527.9, Response filed Apr. 9, 2008 to Communication pursuant to Rules 161 to 182 EPC mailed Mar. 3, 2008, 6 pgs.
European Application Serial No. 10158651.9, Examination Notification Art. 94(3) mailed Jul. 20, 2011, 5 pgs.
European Application Serial No. 10158651.9, Extended European Search Report mailed Jul. 29, 2010, 6 pgs.
European Application Serial No. 10158651.9, Response filed Feb. 28, 2011 to Office Action mailed Sep. 6, 2010, 2 pgs.
European Application Serial No. 10173334.3, Response filed May 23, 2011 to Office Action mailed Nov. 29, 2010, 8 pgs.
International Application Serial No. PCT/US2003/041481, International Search Report mailed Jun. 4, 2004, 7 pgs.
International Application Serial No. PCT/US2006/018497, International Search Report mailed Oct. 24, 2006, 5 pgs.
International Application Serial No. PCT/US2006/018497, Written Opinion mailed Oct. 24, 2006, 7 pgs.
Japanese Application Serial No. 2004-565783, Notice of Allowance mailed Aug. 9, 2010, (W/ English Translation), 4 pgs.
Japanese Application Serial No. 2007-522593, Notice of Allowance mailed Jun. 28, 2011, (W/ English Translation), 6 pgs.
Japanese Application Serial No. 2007-522593, Response filed Jun. 1, 2011 to Non Final Office Action mailed Dec. 27, 2010, (w/ English Translation of Amended Claims), 31 pgs.
Japanese Application Serial No. 2007-551478, Office Action mailed Mar. 4, 2013, (W/ English Partial Translation), 3 pgs.
Japanese Application Serial No. 2007-551478, Office Action mailed Apr. 16, 2012, (W English Translation), 6 pgs.
Japanese Application Serial No. 2007-551478, Office Action mailed Aug. 31, 2011, (w/ Partial English Translation), 5 pgs.
Japanese Application Serial No. 2007-551478, Response filed Nov. 29, 2011 to Office Action mailed Aug. 3, 2011, (W/ English Translation), 12 pgs.
Japanese Application Serial No. 2008-511421, Office Action mailed Nov. 16, 2011, (w/ English Translation), 5 pgs.
Japanese Application Serial No. 2008-511421, Response filed Mar. 14, 2012 to Office Action mailed Nov. 16, 2011, (w/ English Translation of Amended Claims), 16 pgs.
Japanese Application Serial No. 2009-502827, Office Action mailed Jul. 2, 2012, (W/ English Translation), 6 pgs.
Japanese Application Serial No. 2009-502827, Office Action mailed Jul. 19, 2012, (W/ English Translation), 6 pgs.
Japanese Application Serial No. 2009-502827, Office Action mailed Feb. 6, 2012, (W/ English Translation), 7 pgs.
Japanese Application Serial No. 2009-502827, Response filed Apr. 27, 2012 to Office Action mailed Feb. 8, 2012, (W/ English Translation of Claims), 30 pgs.
Japanese Application Serial No. 2009-502827, Response filed Sep. 24, 2012 to Office Action mailed Jul. 19, 2012, (W/ English Translation of Claims), 9 pgs.
Japanese Application Serial No. 2009-510093, Office Action mailed Mar. 12, 2012, (w/ English Translation), 9 pgs.
Japanese Application Serial No. 2009-510093, Response filed Jun. 11, 2012 to Office Action mailed Mar. 12, 2012, (W/ English Translation of Claims), 11 pgs.
Birnbaum, Y, et al., "Ischemic preconditioning at a distance: reduction of myocardial infarct size by partial reduction of blood supply combined with rapid stimulation of the gastrocnemius muscle in the rabbit.", Circulation, 96(5), (Sep. 7, 1997), 1641-6.
Kis, A., et al., "Repeated Cardiac Pacing Extends the Time During Which Canine Hearts are Protected Against Ischaemia-induced Arrhythmias: Role of Nitric Oxide", Journal of Molecular and Cellular, 31(6), (1999), 1229-1241.
Loukogeorgakis, S. P., et al., "Remote ischemic preconditioning provides early and late protection against endothelial ischemia-reperfusion injury in humans: role of the autonomic nervous system.", J Am Coll Cardiol., 46(3), (Aug. 2, 2005), 450-6.
Schoemaker, R. G., et al., "Bradykinin mediates cardiac preconditioning at a distance", Am J Physiol Heart Circ Physiol., 278(5), (May 2000), H1571-6.
Zhi-Qing, Z., et al., "Inhibition of myocardial injury by ischemic postconditioning during reperfusion: comparision with ischemic preconditioning", Am J Physiol Heart Circ Physiol, 285(2), (2003), H579-H588.

* cited by examiner

ISCHEMIA DETECTION USING A HEART SOUND SENSOR

CROSS-REFERENCE TO RELATED APPLICATIONS

This patent application is a continuation of U.S. patent application Ser. No. 12/510,962 filed Jul. 28, 2009, now issued as U.S. Pat. No. 8,034,000, which is a divisional application of U.S. patent application Ser. No. 11/148,107 filed Jun. 8, 2005, now issued as U.S. Pat. No. 7,922,669, which are incorporated herein by reference in their entirety.

This application is related to the following co-pending, commonly assigned U.S. patent application Ser. No. 10/900,570 entitled "DETERMINING A PATIENT'S POSTURE FROM MECHANICAL VIBRATIONS OF THE HEART," filed on Jul. 28, 2004, now issued as U.S. Pat. No. 7,559,901; Ser. No. 10/703,175, entitled "A DUAL USE SENSOR FOR RATE RESPONSIVE PACING AND HEART SOUND MONITORING," filed on Nov. 6, 2003, now issued as U.S. Pat. No. 7,248,923; Ser. No. 10/334,694 entitled "METHOD AND APPARATUS FOR MONITORING OF DIASTOLIC HEMODYNAMICS," filed on Dec. 30, 2002, now issued as U.S. Pat. No. 7,972,275; Ser. No. 10/746,874 entitled "A THIRD HEART SOUND ACTIVITY INDEX FOR HEART FAILURE MONITORING," filed on Dec. 24, 2003, now issued as U.S. Pat. No. 7,115,096; Ser. No. 11/037,275, entitled "METHOD FOR CORRECTION OF POSTURE DEPENDENCE ON HEART SOUNDS," filed on Jan. 18, 2005, now issued as U.S. Pat. No. 7,662,104; Ser. No. 60/631,742 entitled "CARDIAC ACTIVATION SEQUENCE MONITORING FOR ISCHEMIA DETECTION," filed on Nov. 30, 2004; and Ser. No. 11/129,050, entitled "METHOD AND APPARATUS FOR CARDIAC PROTECTION PACING," filed on May 16, 2005, now issued as U.S. Pat. No. 7,917,210, each of which is hereby incorporated by reference.

TECHNICAL FIELD

The field generally relates to implantable medical devices and, in particular, but not by way of limitation, to systems and methods for monitoring the mechanical functions of the heart.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical therapy and to aid a physician or caregiver in patient diagnosis through internal monitoring of a patient's condition. The devices may include electrodes in communication with sense amplifiers to monitor electrical heart activity within a patient, and often include sensors to monitor other internal patient parameters. Other examples of implantable medical devices include implantable diagnostic devices, implantable insulin pumps, devices implanted to administer drugs to a patient, or implantable devices with neural stimulation capability.

Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole. Heart sounds are useful indications of proper or improper functioning of a patient's heart. The present inventors have recognized a need for improved sensing of events related to cardiac activity.

SUMMARY

This document discusses, among other things, systems and methods for monitoring mechanical functions of the heart. A system embodiment includes an implantable medical device (IMD). The IMD includes an implantable heart sound sensor operable to produce an electrical signal representative of at least one heart sound. The heart sound is associated with mechanical activity of a patient's heart. Additionally, the IMD includes a heart sound sensor interface circuit coupled to the heart sound sensor to produce a heart sound signal, and a signal analyzer circuit coupled to the heart sound sensor interface circuit. The signal analyzer circuit is operable to measure a baseline heart sound signal, and to deem that an ischemic event occurred using a measured subsequent change in the heart sound signal from the established baseline heart sound signal.

A method embodiment includes sensing a baseline heart sound signal using an implantable medical device (IMD), sensing at least one subsequent heart sound signal for the patient using the IMD, and deeming that an ischemic event occurred using at least a measured change in at least one heart sound signal from the baseline heart sound signal.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

Because heart sounds are a mechanical measure of a patient's hemodynamic system, monitoring of heart sounds aids caregivers in detecting overall progression of heart disease. For example, for detection of ischemia, an increase in ventricular chamber stiffness and an increase in the degree of restrictive filling are correlated to an increase in loudness of S3 heart sounds. Conversely, because ischemia is associated with a decrease in ventricular chamber contractility, ischemia is correlated to a decrease in the loudness of the S1 heart sound. When S3 heart sounds are present in patients experiencing acute chest pain, such patients are believed to have an increased likelihood of myocardial infarction over other causes of chest pain.

An acute myocardial infarction (AMI) is a complete occlusion of a coronary artery. It is typically caused by a rupture of plaque in a narrowed artery and results in a pronounced change in a patient's hemodynamic system. When at least twenty-five percent of the left ventricle becomes acutely ischemic, the end-diastolic pressure and the end-diastolic volume increase which results in increased loudness of S3 heart sounds, S4 heart sounds, or both S3 and S4 heart sounds, depending on the condition of the heart.

Figure 1:
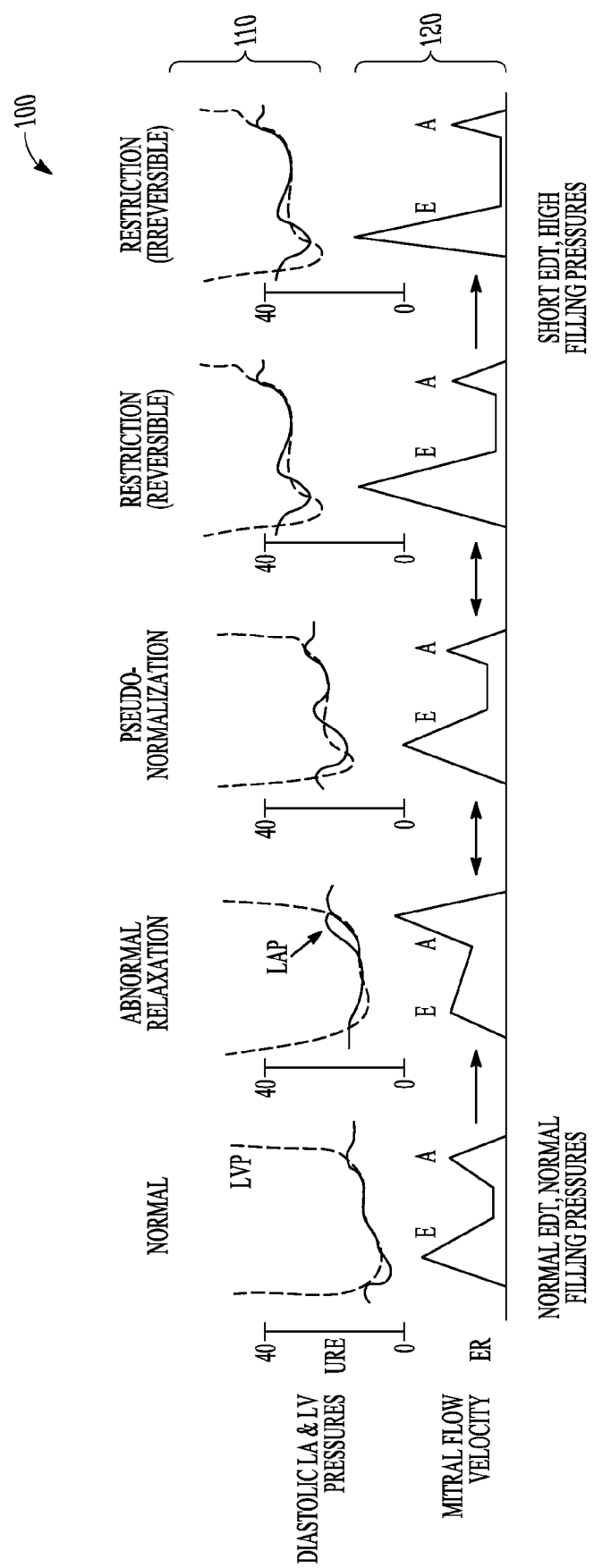
FIG. 1 illustrates an example of progression of heart failure.

FIG. 1 illustrates an example of changes in diastolic pressure with worsening heart failure (HF). The Figure shows graphs 110 of left atrium (LA) and left ventricle (LV) diastolic pressures and graphs 120 of the associated E-wave and A-wave. An E-wave refers to the peak mitral flow velocity during passive filling, and an A-wave refers to the peak mitral flow velocity during atrial contraction. The graphs 100 represent stages of worsening HF from a normal case on the left to irreversible flow restriction on the right. As the HF condition worsens, the filling time shortens and the left ventricular pressure (LVP) and left atrial pressure (LAP) become more elevated. Depending on the condition of the heart, this results in increased loudness of S3 heart sounds, S4 heart sounds, or both S3 and S4 heart sounds. If a baseline of heart sound measurements for a patient is established, a change from the baseline is a good indication that something has changed in the hemodynamic system of the patient.

The progression of HF is typically accompanied by changes in heart sounds over time. First, an S4 heart sound may develop while the heart is still relatively healthy. Second, the S4 heart sound becomes more pronounced. Third, as deterioration of the left ventricle continues, S3 heart sounds become more pronounced. Sometimes, this is accompanied by a decrease in S1 heart sounds due to a decrease in the heart's ability to contract. Thus, ongoing or continuous monitoring of heart sounds would greatly assist caregivers in monitoring heart disease. However, individual patients may exhibit unique heart sounds that complicate a generalized approach to heart sound monitoring. For example, the mere presence of an S4 heart sound is not necessarily indicative of heart disease because normal patients may have an S4 heart sound. Another complication develops if a patient experiences atrial fibrillation when an ischemia occurs. In this case a strong atrial contraction, and the associated S4 heart sound, is likely to be absent due to the atrial fibrillation. This results in an increase in the S3 heart sound without an associated S4 heart sound or without an increase in an S4 heart sound. Therefore, the progression of heart disease, such as HF and an ischemic event, is typically better monitored by establishing a patient-specific control baseline heart sound measurement and then monitoring for changes from that baseline. The baseline could be established in one or several different criteria, such as at particular physiologic or pathophysiologic state, at a specific posture, at a particular time of day, etc.

Changes due to AMI are immediate and result in a heart sound change within seconds or minutes. In contrast, heart sound changes due to worsening HF are gradual and occur over hours or days. Therefore, not just the change but the timeframe of the occurrence of the change in heart sounds can be used to detect overall progression of heart disease. Additionally, relationships between heart sounds can be used to determine the likelihood of an ischemic event. For example, the dynamics between the S3 and S4 heart sounds with respect to the HF progression can be used to determine the likelihood that a patient experienced an ischemic event. An appearance of the S3 and S4 heart sounds is more likely to indicate a recent occurrence of an ischemic event if the S4/S3 ratio is high than if the S4/S3 ratio is low, which would instead indicate that a patient is in a more advanced stage of HF.

Implantable medical devices (IMDs) can include sensors to monitor internal patient parameters such as heart sounds. Typically, the heart sound sensor is an accelerometer monitoring the vibrations associated with heart sounds. Because the devices are implantable, they can be used to provide ongoing or continuous ambulatory monitoring of a patient's heart sounds. The implanted device is used to first establish a baseline for its individual patient during a pre-AMI period. The device then monitors the patient heart sounds to detect changes from the baseline.

Figure 2:
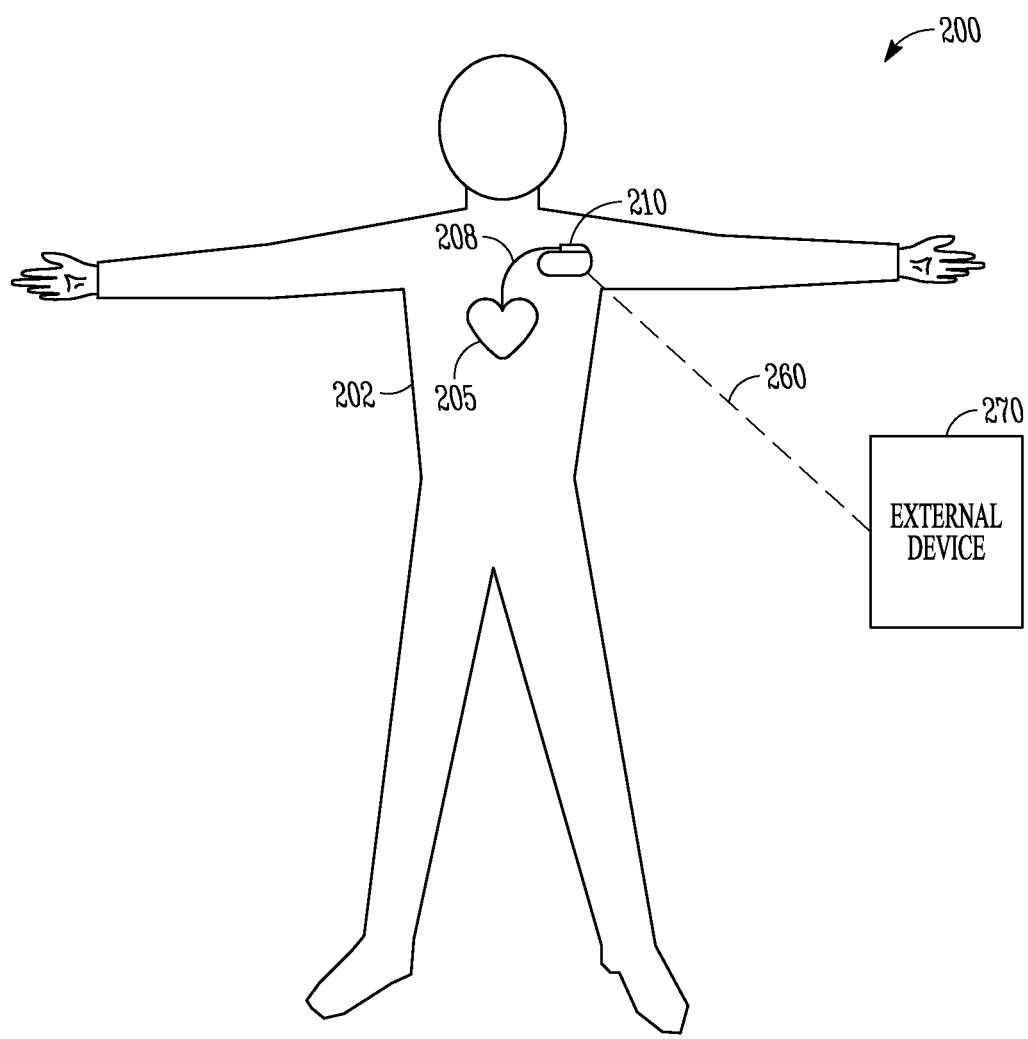
FIG. 2 illustrates an embodiment of portions of a system that uses an implantable medical device.

FIG. 2 illustrates an embodiment of a system 200 that uses an IMD 210. The system 200 shown is one embodiment of portions of a system 200 used to treat a cardiac arrhythmia or otherwise improve heart function. A pulse generator (PG) or other IMD 210 is coupled to a heart 205 of a patient 202 by a cardiac lead 208, or additional leads. A leadless IMD is also possible. Examples of IMD 210 include, without limitation, a pacer, a defibrillator, a cardiac resynchronization therapy (CRT) device, or a combination of such devices. Other examples include implantable diagnostic devices, a drug pump, and a neural stimulation device. System 200 also typically includes an IMD programmer or other external system 270 that provides wireless communication signals 260 to communicate with the IMD 210, such as by using radio frequency (RF) or other telemetry signals.

In FIG. 2, cardiac lead 208 includes a proximal end that is coupled to IMD 210 and a distal end, coupled by an electrode or electrodes to one or more portions of a heart 205. The electrodes typically deliver cardioversion, defibrillation, pacing, resynchronization therapy, or combinations thereof to at least one chamber of the heart 205. IMD 210 includes components that are enclosed in a hermetically-sealed canister or "can." Additional electrodes may be located on the can, or on an insulating header, or on other portions of IMD 210, such as for providing unipolar pacing and/or defibrillation energy, for example, in conjunction with the electrodes disposed on or around heart 205. The lead 208 or leads and electrodes are also typically used for sensing electrical activity of a heart 205, or other.

Implantable heart sound sensors are generally implantable acoustic sensors that convert the detected sounds of the heart into an electrical signal representative of the heart sounds. Typically, an acoustic sensor for an IMD 210 includes an accelerometer mounted within the can. In another sensor example, a microphone is located within the can. In another example, the sensor includes a strain gauge.

Figure 3:
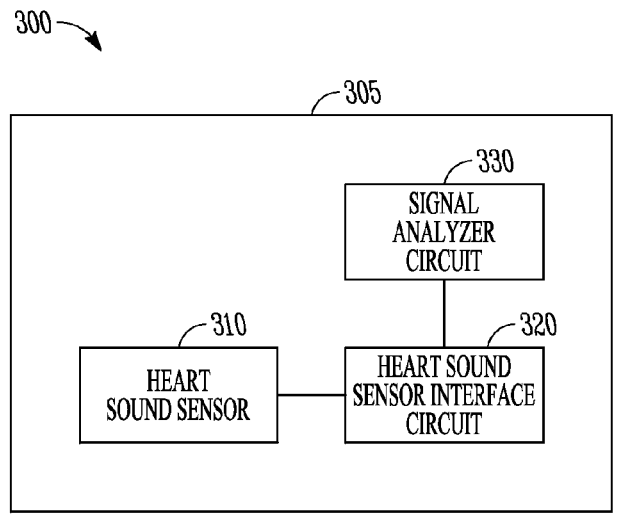
FIG. 3 shows portions of an embodiment of a system for monitoring heart sounds.

FIG. 3 shows portions of an embodiment of a system 300 for monitoring heart sounds. The system 300 includes an implantable medical device (IMD) 305. The IMD 305 includes an implantable heart sound sensor 310, a heart sound sensor interface circuit 320 coupled to the heart sound sensor 310, and a signal analyzer circuit 330 coupled to the heart sound sensor interface circuit 320. The heart sound sensor 310 produces an electrical signal representative of at least one heart sound. The heart sound sensor interface circuit 320 provides a heart sound signal to the signal analyzer circuit 330. The signal analyzer circuit 330 measures a baseline heart sound signal, such as by being operable to perform an algorithm or algorithms implemented by hardware, software, firmware or any combination of hardware, software or firmware. In some examples, the baseline heart sound signal is an aggregate of a patient's different heart sound signals that occur during a cardiac cycle. In another example, the baseline signal represents a subset of the heart sounds, such as one type of heart sound. In one example, the baseline heart sound signal is established for an individual patient during a pre-AMI period. In another example, the baseline is established at time of implant. In yet another example, the baseline is established while a patient is in a predetermined physiologic or pathophysiologic state.

In some examples, the signal analyzer circuit 330 includes an averaging circuit and establishes a baseline heart sound signal by forming an ensemble or other average of multiple sampled values of like heart sound signals. One example of descriptions of systems and methods for obtaining ensemble averages of heart sound signals is found in the commonly assigned, co-pending U.S. patent application Ser. No. 10/746,874 by Siejko et al., entitled "A Third Heart Sound Activity Index for Heart Failure Monitoring," filed on Dec. 24, 2003, which is incorporated herein by reference. In some examples, the signal analyzer circuit 330 includes a low pass filtering circuit. In some examples, the signal analyzer circuit 330 includes a central tendency circuit and establishes a baseline signal by determining the central tendency of multiple sampled values of the heart sound signals. The baseline signal is stored in memory in, or coupled to, the signal analyzer circuit 330. In some examples, the baseline signal is loaded into the memory using an external device to communicate with the IMD 305. After the baseline is established, the signal analyzer circuit 330 monitors one or more heart sound signals for any change from the baseline signal. In some examples, the baseline signal is an aggregate of a patient's different heart sound signals and the change includes a change from that aggregate of signals. In some examples, the baseline signal represents a subset of the heart sounds that occur during a cardiac cycle, such as one type of heart sound, and the change includes a change in the one type of heart sound from the baseline heart sound. In some examples, a sampled segment of the heart sound signal that includes the change is stored in the memory. Some examples of the sampled segment include a segment sampled before the change occurred and a segment sampled after the change occurred. Upon a particular of change, the signal analyzer circuit 330 deems that a patient has experienced an ischemic event, such as an acute myocardial infarction.

Once the signal analyzer 330 deems that such an event has occurred, this information can then be used by the signal analyzer circuit 330 to provide an indication of the event. In one example, the signal analyzer circuit 330 activates an alarm, such as a buzzer or other audible indication in the IMD 305, to indicate that an ischemic event occurred. In another example, the IMD 305 includes a communication circuit coupled to the signal analyzer circuit 330 and the IMD 305 communicates information about the measured change from the baseline in the heart sound signal to an external device. In some examples, the external device initiates measurements of the heart sound signals. In some examples, the IMD 305 transmits the signal segment stored in memory to the external device. In some examples, the external device is an IMD programmer and the IMD 305 indicates that an ischemic event has occurred by setting a status indication readable by the programmer upon a subsequent interrogation of the IMD 305. In another example, the external device is a repeater that retransmits information from the IMD 305 over a network. In some examples, the external device is in communication with the IMD 305 and a computer network such as a hospital network or the Internet. The indication of the ischemic event or an alarm can then be transmitted to a caregiver using the network. An indication or alarm provided to the patient has further uses, such as to direct the patient to take a drug, adjust medication, or to seek immediate medical assistance.

Figure 4A:
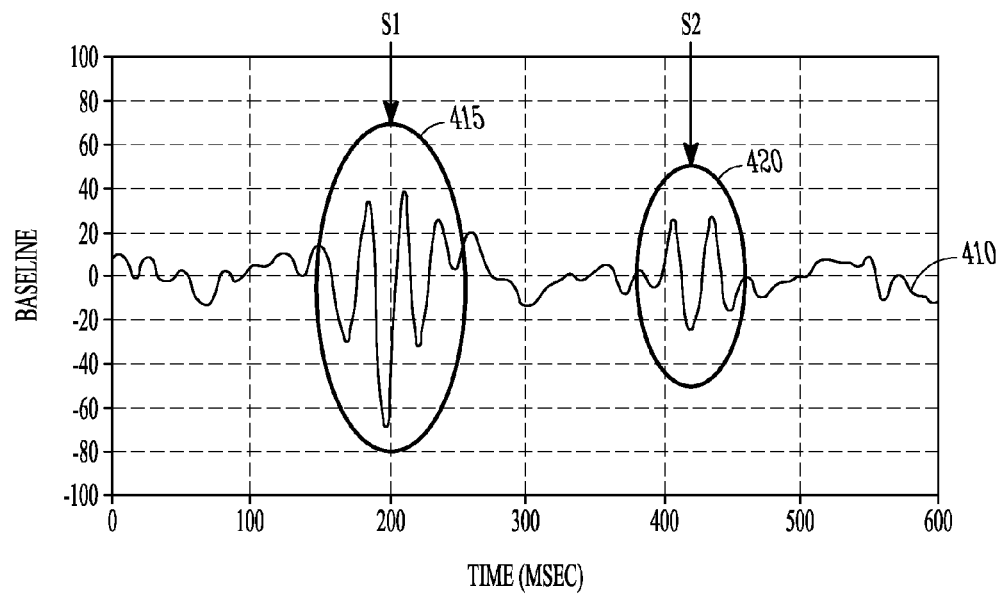
FIGS. 4A-C illustrate heart sound signals obtained from an animal study.
Figure 4B:
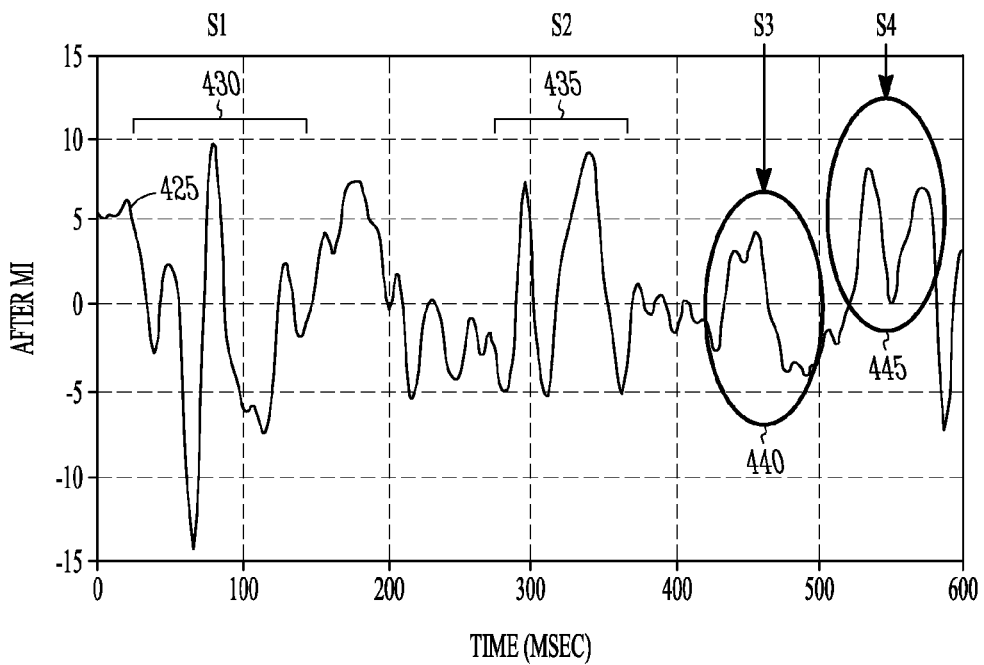
Figure 4C:
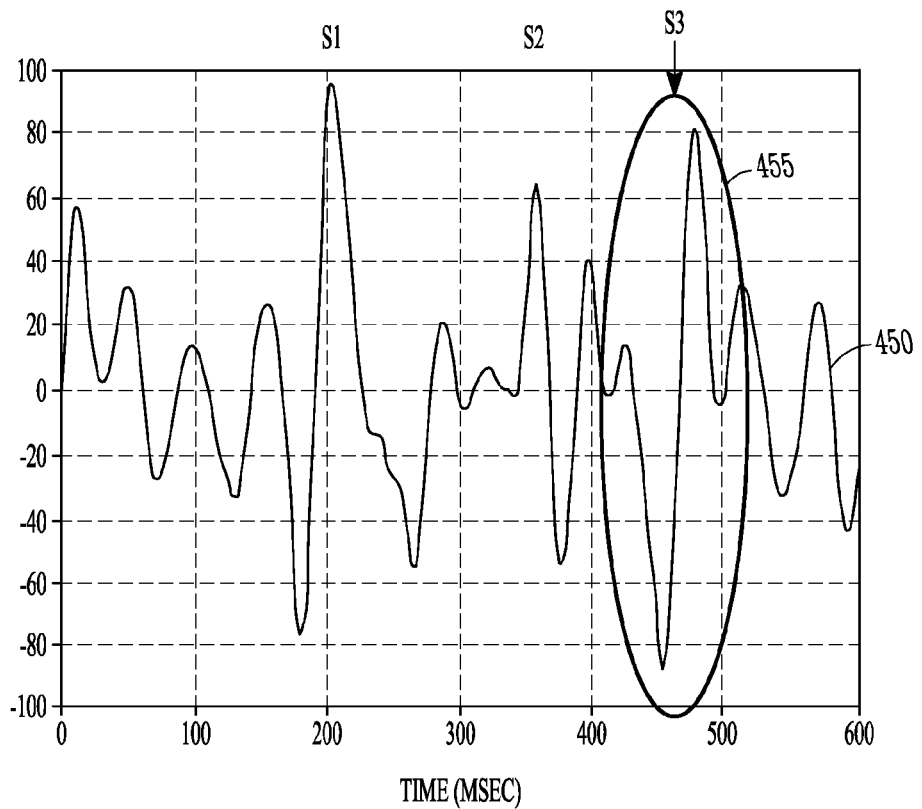

Ischemic events can be detected from a variety of different measured changes from one or more baseline heart sound signals. An example is shown in FIGS. 4A-4C, which illustrate heart sound signals obtained from an animal study. FIG. 4A shows an example of a baseline heart sound signal 410 obtained for an animal that was measured using an implanted accelerometer-type heart sound sensor. The signal 410 includes the S1 heart sound 415 and the S2 heart sound 420. FIG. 4B shows an example of a measured heart sound signal 425 after ischemia was induced in the animal by microembolization. The signal 425 includes the S1 heart sound 430, an S2 heart sound 435, and further shows the presence of the S3 heart sound 440 and the S4 heart sound 445. FIG. 4C shows an example of a heart signal 450 after the animal decompensated. FIG. 4C shows that the amplitude of the S3 heart sound 455 has increased from FIG. 4B, and the amplitude of the S3 heart sound has changed relative to the S1 and S2 heart sounds. FIGS. 4A-C show that in some examples, an ischemic event results in the presence of at least one heart sound in the measured signal 425, 450, such as the S3 or S4, which is absent from the baseline heart sound signal 410. In some examples, an ischemic event results in a reduction in amplitude of at least one heart sound, such as the S1 or S2 heart sound, in the measured signal 425, 450 compared to the baseline heart sound signal 410. In some examples, the signal analyzer circuit 330 deems that an ischemic event has occurred from the duration of an occurrence of a heart sound, such as the S3 or S4 heart sound, that is absent from the baseline heart sound signal 410. In some examples, the signal analyzer circuit 330 deems that an ischemic event has occurred from the frequency of re-occurrence of a heart sound, such as the S3 or S4 heart sound, that is absent from the baseline heart sound signal 410.

In some system examples, the signal analyzer circuit 330 deems that an ischemic event has occurred by measuring a change in amplitude of the measured heart sound signal from the amplitude of a baseline heart sound signal. The signal analyzer circuit 330 measures the amplitude of a particular type of heart sound, such as the S1, S2, S3, or the S4 heart sound, and compares the measured amplitude to its corresponding baseline amplitude. However, not all patients will exhibit an S3 or S4 heart sound substantially all or most of the time. In some examples, the measured change is deemed to result from an ischemic event if the measured change is a specified increase in amplitude of an S3 or S4 heart sound from the corresponding baseline amplitude. In some examples, if the change in amplitude is at least a specified percentage increase from the corresponding baseline amplitude, an ischemic event is deemed to have occurred. In some examples, the measured change is deemed to result from an ischemic event if the measured change is a specified decrease in amplitude of an S1 or S2 heart sound from the corresponding baseline amplitude.

In some examples, the signal analyzer circuit 330 establishes a baseline amplitude of a first heart sound normalized with respect to a second heart sound. Such normalization includes calculating a ratio between at least two different heart sounds associated with the same cardiac cycle. The signal analyzer circuit 330 deems that an ischemic event occurred when it measures a change in the ratio from a ratio of the corresponding baseline amplitude, such as, for example, a percentage increase in the ratio from the corresponding baseline ratio. In one example, the amplitude of the S3 or S4 heart sound is normalized with respect to the amplitude of the S1 or S2 heart sound. Because some ischemic events are associated with both an increase in the amplitude of the S3 or S4 heart sound and a decrease of the S1 or S2 heart sound, an advantage of using normalization is that it is more sensitive to some types of ischemic changes than an amplitude measurement alone. In another example, the amplitude of the S4 heart sound is normalized with respect to the S1 heart sound. In another example, the amplitude of the S4 heart sound is normalized with respect to the S3 heart sound to provide an indication of the relative changes between the S3 and S4 heart sound. If the normalization includes a ratio of the heart sounds (S4/S3), in the early stages of heart disease the ratio increases with the increase in the S4 heart sound. Later, the ratio decreases due to the later increase in the S3 heart sound. In some examples, the amplitude of the S1, S3, or S4 heart sound is normalized with respect to the amplitude of the S2 heart sound.

In some examples, the signal analyzer circuit 330 includes a frequency analyzer circuit. This permits the signal analyzer circuit 330 to establish a baseline power spectrum of a heart sound, such as the S1, S2, S3, or S4 heart sound, by calculating the power in the heart sound signal in several frequency bands. The signal analyzer circuit 330 deems that an ischemic event has occurred by measuring a change in the power spectrum of a heart sound signal from the corresponding baseline power spectrum. In some examples, the signal analyzer circuit 330 deems that an ischemic event occurred using a heart sound amplitude measurement that is normalized with respect to the calculated power in the signal. In the normalization, a power of the heart sound signal is calculated in several frequency bands. The calculated power of a specific portion or portions of the signal is used to normalize the amplitude. As an example, the power calculated from a high frequency band of a heart sound signal sensed during systole can be used to normalize the amplitude of the heart sound.

In some examples, the IMD 305 includes a posture sensor, and the IMD 305 measures heart sound signals in association with a posture of a patient. For example, heart sound signals are only measured or used while the patient is in a particular posture (e.g., upright), or measurements made while the patient is in one posture (e.g., upright) are distinguished from measurements made while the patient is in another posture (e.g., lying down). This removes a source of variability of the heart sound signals due to patient posture. A description of systems and methods for monitoring heart sounds in association with patient posture are found in commonly assigned, co-pending U.S. patent application Ser. No. 11/037,275 by Siejko et al., entitled "Method for Correction of Posture Dependence on Heart Sounds," filed on Jan. 18, 2005, which is incorporated herein by reference.

In some examples, the IMD 305 measures heart sounds in association with patient activity. To detect patient activity, some examples of the IMD 305 include a patient activity sensor. If the heart sound sensor is an accelerometer, the activity sensor can be a second accelerometer or the same accelerometer as the heart sound sensor. In some examples, the IMD 305 infers the patient's activity level from a patient's heart rate, respiration rate, or minute ventilation such as by using a thoracic impedance sensor. In some examples, the IMD 305 deems that an ischemic event has occurred using a measured change in the heart sound signal from at least one corresponding baseline heart sound signal specifically established for exercise conditions. An early or mid-diastolic merging of S3 and S4 heart sounds (i.e., a gallop rhythm) developing after exercise is believed to nearly always signify myocardial disease with reduced myocardial function. Thus, in some examples, an ischemic event can be detected by the presence of the gallop rhythm that is absent from the baseline heart sound signal.

In some examples, the signal analyzer circuit 330 uses the temporal nature of changes in one or more heart sounds to distinguish between an ischemic event and an indication of a worsening condition of HF decompensation. For example, if the measured change from the baseline heart sound signal occurs relatively suddenly with a time constant that ranges from a few seconds to a few minutes (e.g., five minutes), the episode is deemed to be an ischemic event. If the measured change from the baseline heart sound signal occurs with a time constant of several hours (e.g., four hours) or days, the episode is deemed to be an indication of a worsening condition of HF decompensation. In some examples, the signal analyzer circuit 330 activates a same or different alarm to indicate the worsening condition of congestive heart failure. In some examples, the signal analyzer circuit 330 stores data associated with measured changes from the baseline signal in memory. The signal analyzer circuit 330 is capable of calculating trend data of the measured changes and storing the trend data in memory. In some examples, the signal analyzer circuit 330 uses the trend data to generate a congestive heart failure status indication. In some examples, the IMD 305 transmits the trend data to an external device, such as for display.

Figure 5:
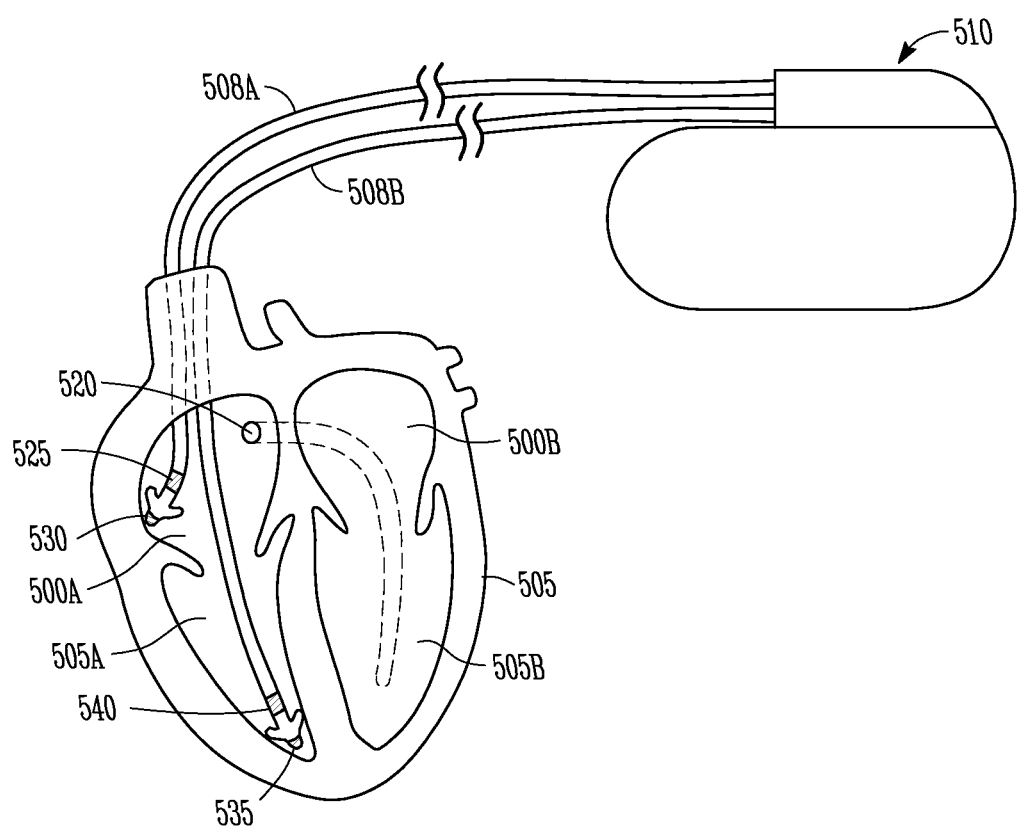
FIG. 5 illustrates an embodiment of an implantable medical device coupled by leads to a heart.

FIG. 5 illustrates an IMD 510 coupled to heart 505, such as by one or more leads 508A-B. Heart 505 includes a right atrium 500A, a left atrium 500B, a right ventricle 505A, a left ventricle 505B, and a coronary vein 520 extending from right atrium 500A. In this embodiment, atrial lead 508A includes electrodes (electrical contacts, such as ring electrode 525 and tip electrode 530) disposed in, around, or near an atrium 500A of heart 505 for sensing signals, or delivering pacing therapy, or both, to the atrium 500A. Lead 508A optionally also includes additional electrodes, such as for delivering atrial cardioversion, atrial defibrillation, ventricular cardioversion, ventricular defibrillation, or combinations thereof to heart 505. Lead 508A optionally further includes additional electrodes for delivering pacing or resynchronization therapy to the heart 505.

Ventricular lead 508B includes one or more electrodes, such as tip electrode 535 and ring electrode 540, for sensing signals, for delivering pacing therapy, or for both sensing signals and delivering pacing therapy. Lead 508B optionally also includes additional electrodes, such as for delivering atrial cardioversion, atrial defibrillation, ventricular cardioversion, ventricular defibrillation, or combinations thereof to heart 505. Such electrodes typically have larger surface areas than pacing electrodes in order to handle the larger energies involved in defibrillation. Lead 508B optionally further includes additional electrodes for delivering pacing or resynchronization therapy to the heart 505.

Other forms of electrodes include meshes and patches which may be applied to portions of heart 505 or which may be implanted in other areas of the body to help "steer" electrical currents produced by IMD 510. In one embodiment, one of atrial lead 508A or ventricular lead 508B is omitted, i.e., a "single chamber" device is provided, rather than the dual chamber device illustrated in FIG. 5. In another embodiment, additional leads are provided for coupling the IMD 510 to other heart chambers and/or other locations in the same heart chamber as one or more of leads 508A-B. The present methods and systems will work in a variety of configurations and with a variety of electrical contacts or "electrodes," including a leadless system that uses electrodes remote from, rather than touching, the heart 505.

Figure 6:
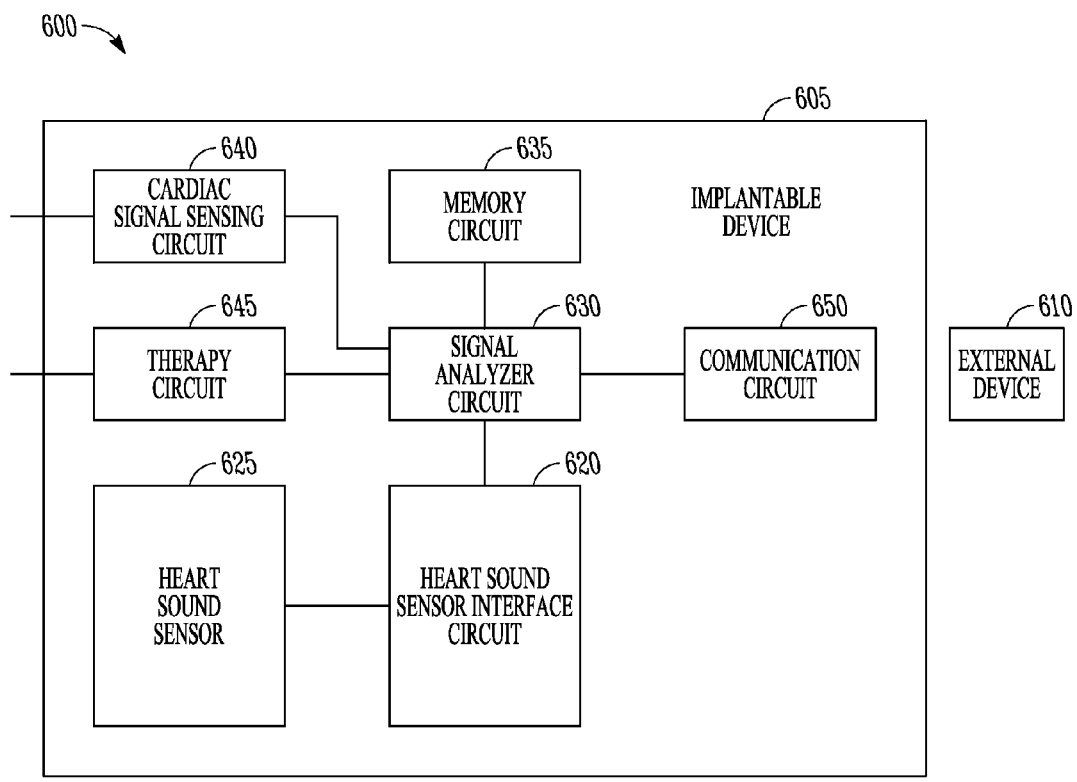
FIG. 6 shows portions of an embodiment of a system for monitoring heart sounds and electrocardiograms.

FIG. 6 shows portions of an example of a system 600 for monitoring heart sounds and electrical cardiac signals. In this example, the system 600 includes an IMD 605 and an external device 610 operable to communicate with the IMD 605. The IMD 605 includes a heart sound sensor 625 and a heart sound sensor interface circuit 620 coupled to a signal analyzer circuit 630. The heart sound sensor 625 produces electrical signals representative of at least one heart sound. The IMD 605 also includes a memory circuit 635, a cardiac signal sensing circuit 640, and a therapy circuit 645.

The therapy circuit 645 is coupled to one or more electrodes. In one example, the therapy circuit 645 is attached to a cardiac lead or leads such as to provide cardioversion, defibrillation, pacing, resynchronization therapy, or one or more combinations thereof to at least one chamber of the heart. The memory circuit 635 stores heart sound measurements. In some examples, the memory circuit 635 also stores segments of measured cardiac signals. The IMD 605 further includes a communication circuit 650. The external device 610 communicates wirelessly with the IMD 605 by using RF or other telemetry signals. The IMD 605 communicates heart sound information to the external device 610. In some examples, the external device 610 is part of, or is in communication with, a computer network such as a hospital computer network or the Internet.

The cardiac signal sensing circuit 640 senses electrical cardiac signals associated with the action potential signals of a heart. The action potentials propagate through the heart's electrical conduction system to excite various regions of myocardial tissue. The sensing circuit 640 provides an electrical signal representative of such signals. Examples of cardiac signal sensing circuits 640 include, without limitation, a subcutaneous electrocardiogram (ECG) sensing circuit, an intracardiac electrogram (EGM) sensing circuit, and a wireless ECG sensing circuit. In a subcutaneous ECG sensing circuit, electrodes are implanted beneath the skin and the ECG signal obtained is referred to as subcutaneous ECG or far-field electrogram. In an intracardiac EGM circuit, at least one electrode is placed in or around the heart. A wireless ECG includes a plurality of electrodes to provide differential sensing of cardiac signals to approximate a surface ECG. Descriptions of wireless ECG systems are found in commonly assigned, co-pending U.S. patent application Ser. No. 10/795,126 by McCabe et al., entitled "Wireless ECG in Implantable Devices," filed on Mar. 5, 2004, which is incorporated herein by reference.

The signal analyzer circuit 630 measures the heart sound signal and the cardiac signal. In some embodiments, the signal analyzer circuit 630 measures the heart sounds in correspondence with a sensed heart depolarization, such as to help identify particular heart sounds. The desired heart sound is identified by aligning the heart sound signal to known features in a sensed cardiac signal. For example, an R-wave sensed by the cardiac signal sensing circuit 640 helps align S1 and S2 heart sounds sensed with the heart sound sensor 625. This is useful for, among other things, identifying a time window associated with a particular heart sound, such as when establishing a baseline heart sound signal.

In some examples, the IMD 605 deems that an ischemic event occurred using either the cardiac signal or the heart sound signal. In some examples, the IMD 605 deems that an ischemic event occurred using both a measured change in the cardiac signal from an established baseline cardiac signal and a measured change in the heart sound signal from an established corresponding baseline heart sound signal. Using both signals to conclude that an ischemic event occurred increases the confidence or specificity in the conclusion. As an example, the signal analyzer circuit 630 deems that an ischemic event has occurred using a specified measured minimum change from the corresponding baseline heart sound signal and a sensed cardiac signal having an S-wave to T-wave ("ST") interval that deviates by at least a specified amount from an ST interval of a baseline cardiac signal. In another example, the signal analyzer circuit 630 deems an ischemic event to have occurred upon detecting at least a specified measured change in the heart sound signal and a sensed cardiac signal having a T-wave that is inverted from the T-wave in the baseline cardiac signal. In another example, the signal analyzer circuit 630 deems an ischemic event to have occurred upon detecting at least a specified measured change in the heart sound signal and a sensed cardiac signal having a sensed T-wave that is biphasic relative to a monophasic T-wave in the baseline cardiac signal. Descriptions of systems and methods for detecting ischemia using wireless ECG circuits are found in commonly assigned, co-pending U.S. Patent Application Ser. No. 60/631,742 by Zhang et al., entitled "Cardiac Activation Sequence Monitoring for Ischemia Detection," filed on Nov. 30, 2004, which is incorporated herein by reference.

In some examples, a surface ECG sensing circuit is coupled to the external device. The ECG sensing circuit includes at least two electrodes attached to the skin of a patient to sense cardiac signals. The external device then deems that an ischemic event occurred using both a measured change in an ECG signal obtained from the external ECG circuit and a measured change in the heart sound signal obtained from the IMD 605.

In some examples, the signal analyzer circuit 630 deems that an ischemic event has occurred using a temporal relationship between the measured change in the heart sound signal and the sensed event indicated by the cardiac signal. In one such example, the signal analyzer circuit 630 deems an ischemic event to have occurred by detecting a sequence in time of heart sound signal changes and cardiac signal changes. As an illustrative example of such a sequence of events, the signal analyzer circuit 630 may first measure a decrease in the S1 heart sound signal from the S1 baseline. The signal analyzer circuit 630 subsequently measures a deviation in the ST interval of the cardiac signal from the baseline cardiac signal. Later, an S3 heart sound appears on the measured heart sound signal, where the S3 heart sound is absent in the baseline heart sound signal. When such a sequence occurs, the signal analyzer circuit 630 deems that an ischemic event has occurred. As another example, the cardiac signal T-waves discussed above typically disappear after about one hour following an ischemic event, but the evidence from heart sound changes remains. In one example, the signal analyzer circuit 630 deems that an ischemic event has occurred when the cardiac signal feature appears temporarily (e.g., for a time period of less than about one hour), but the heart sound signal changes from baseline persist, even after the temporary cardiac signal feature subsides.

In some examples, the signal analyzer circuit 630 uses rules to combine the outputs of the cardiac sensing circuit 640 and the heart sound sensor circuit 620. In one example, the signal analyzer circuit 630 assigns at least a first weight to the measured change from baseline in the heart sound signal and assigns at least a second weight to a sensed event indicated by the change in the ECG signal. The signal analyzer circuit 630 then deems an ischemic event to have occurred according to at least one rule incorporating the measured change in the heart sound signal, the sensed event indicated by the ECG signal and the assigned weights. Table 1 below shows an example where the rule applied is a decision matrix. The signal analyzer circuit 630 applies a low, medium, or high weight to the strength of a measured S4 heart sound change. Similarly, the signal analyzer circuit 630 applies a low, medium, or high weight to a measured deviation in an ST interval in an ECG signal. In one example, the weights are applied based on amplitude changes from a corresponding patient-specific baseline.

TABLE 1

| | ST deviation | | |
|---|---|---|---|
| High | — | — | High Confidence Level |
| Medium | — | — | — |
| Low | Low Confidence Level | — | — |
| | Low | Medium | High |

S4 Heart Sound

If the weights of the measured signals are both low, the signal analyzer circuit 630 has a low confidence level that an ischemic event occurred. If the weights of the measured signals are both high, the signal analyzer circuit 630 has a high confidence level that an ischemic event occurred. The rest of the decision matrix can be programmed based on factors such as history of the patient or experience of the caregiver.

In some examples, the IMD 605 includes one or more other sensors, such as to measure intracardiac or trans-thoracic impedance, or blood pressure. In some examples, the signal analyzer circuit 630 uses at least one rule to blend the outputs of the various sensors to make a decision as to whether a patient has experienced an ischemic event. In some examples, the signal analyzer circuit 630 assigns weights to corresponding outputs of the sensors, and applies at least one rule to merge the sensor outputs and the measured change in the heart sound signal using the weights. The signal analyzer circuit 630 determines whether an ischemic event occurred based on the application of the rule. In some examples, the signal analyzer circuit 630 applies one or more fuzzy logic rules that use the weights to merge the sensor outputs and the measured change in the heart sound signal to determine whether an ischemic event occurred.

In some examples, the signal analyzer circuit 630 discriminates a transient ischemic event from an AMI event using a measured change in a heart sound signal from an established baseline heart sound signal. Sometimes an ischemic event detectable by the system 600 may be a transient ischemic. Transient ischemic events can occur in non-emergency situations, such as a result of exercise for example. In one system example, the signal analyzer circuit 630 discriminates a transient ischemic event from an AMI event based on the duration of the measured subsequent change from the established heart sound signal. As an illustrative example, the signal analyzer circuit 630 deems an ischemic event a transient event when a heart sound (such as an S3 or S4 heart sound, or a combination of S3 and S4 heart sounds) not present in the established baseline signal briefly appears and then disappears from the heart sound signal. In another system example, the signal analyzer circuit 630 discriminates a transient ischemic event from an AMI event based on a change in amplitude of a heart sound. As an illustrative example, the signal analyzer circuit 630 may deem that a change in amplitude is a transient ischemic event if the amplitude change is below a predetermined threshold change value and an AMI event if the change is above the change value.

In yet another system example, the signal analyzer circuit 630 discriminates a transient ischemic event from an AMI event based on a temporal relationship of a sensed event indicated by a sensed cardiac signal and the measured subsequent change in the heart sound signal from the established baseline heart sound signal. For example, if the signal analyzer circuit 630 detects a change in both the cardiac signal and the heart sound signal, but the cardiac signal change goes away while the heart sound change remains, the signal analyzer circuit 630 deems the event an AMI event. If the signal analyzer circuit 630 detects a change in the cardiac signal but the heart sound signal does not change, the signal analyzer circuit 630 deems the event a transient ischemic event. In some examples of the system 600, an indication of AMI events or both indications of AMI events and transient ischemic events are stored in the memory 635, communicated to the external device 610, or both stored in the memory 635 and communicated to the external device 610.

Figure 7:
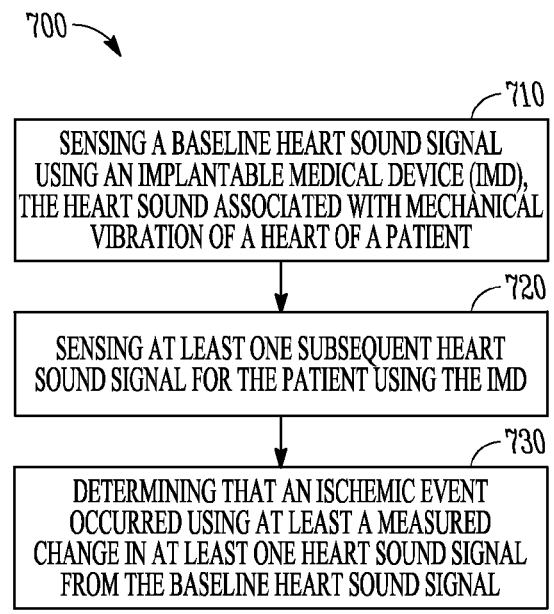
FIG. 7 is a block diagram of a method of detecting ischemia using a heart sound sensor.

FIG. 7 is a block diagram of a method 700 of detecting ischemia using a heart sound sensor. At 710, a baseline heart sound signal is sensed using an IMD. The heart sound or sounds are associated with mechanical vibrations of a heart of a patient. At 720, at least one subsequent heart sound signal for the patient is sensed using the IMD. In some examples of the method, the baseline heart sound signal and subsequent heart sound signal are sensed in association with a posture of a patient to remove the variability of the heart sound signal measurements with patient posture. At 730, an ischemic event is deemed to have occurred using at least a measured change in at least one heart sound from the corresponding baseline heart sound signal. In some examples, the heart sounds are continuously, or occasionally, monitored for changes from the corresponding baseline.

According to some examples, an occurrence of an ischemic event is inferred from a measured increase in amplitude of a heart sound from a baseline heart sound amplitude. In some examples, the baseline includes sampled amplitudes stored in a memory. In some examples, the ischemic event is inferred using a measured decrease in amplitude of a heart sound from a baseline heart sound amplitude. In some examples, the ischemic event is inferred using a measured increase in amplitude of a first heart sound and a measured decrease in a second heart sound. In some examples, a normalization of a first heart sound with respect to a second heart sound is monitored. As an example, an occurrence of an ischemic event is inferred from an increase in the ratio measured relative to a baseline value of the S3/S1 ratio. As another example, the ratio of the S4 amplitude to the S3 amplitude is monitored. An occurrence of an ischemic event is inferred from an increase in the ratio measured relative to a baseline value of the S4/S3 ratio. In yet another example, the amplitude of the S1, S3, or S4 heart sound is normalized with respect to the S2 heart sound.

In some examples, an ischemic event is deemed to have occurred by the appearance of a transient heart sound that is missing in the baseline heart sound signal. For example, if the baseline heart sound signal has an absence of S3 heart sounds, an ischemic event is inferred when at least one transient S3 heart sound is detected in the signal. As another example, if the baseline heart sound signal has an absence of S4 heart sounds, an ischemic event is inferred when at least one transient S4 heart sound is detected in the signal. In some examples, an ischemic event is deemed to have occurred based on the frequency with which a heart sound missing in the baseline heart sound signal appears in the measured signals and then disappears. In some examples, an ischemic event is deemed to have occurred based on the time duration that a heart sound missing in the baseline heart sound signal appears in the measured signals before it disappears. In some examples, an ischemic event is inferred when a merging of S3 and S4 heart sounds is detected in the heart sound signal. In an example, an ischemic event is inferred when the merging occurs at high heart rates when the time for diastole is shortened, such as at one hundred beats per minute (100 bpm) or higher.

According to some examples, frequency components of heart sounds and the power component of the signal at the frequencies are monitored, i.e., a power spectrum is monitored. A baseline of the power spectrum of at least one heart sound, such as the S3 or S4 heart sound, is established, such as by using a fast Fourier transform (FFT) provided by digital signal processing (DSP). An occurrence of an ischemic event is inferred from a measured change in the power spectrum of a heart sound signal from the corresponding baseline power spectrum. In some examples, an occurrence of an ischemic event is inferred from the amplitude of a heart sound normalized with respect to the power in the heart sound signal. In some examples, the method 700 further includes activating an alarm to indicate that an ischemic event occurred. The alarm includes an audible or vibrating alarm from the IMD, or an alarm from an external device. The external device may receive an alarm status from the IMD when the IMD is next interrogated or by a communication originating from the IMD. The alarm may be used to notify the patient, a caregiver, or both a patient and caregiver of the ischemic event.

According to some examples, an occurrence of an ischemic event is inferred using both a cardiac signal sensed by the IMD and the measured change in the heart sound signal. In some examples, the inference is made when a measured change from established baseline signals occurs in both the cardiac signal and the heart sound signal. In some examples, an ischemic event is inferred from timing relationships between the change or changes on the cardiac signal and the change or changes in the heart sound signals. In some examples, an ischemic event is inferred using the temporal relationship of a sensed event indicated by the sensed cardiac signal and the measured change in the heart sound signal from the established baseline heart sound signal. As an illustrative example, an ischemic event is inferred when the sensed event is no longer indicated by the sensed cardiac signal while the measured change in the heart sound signal continues to persist.

Figure 8:
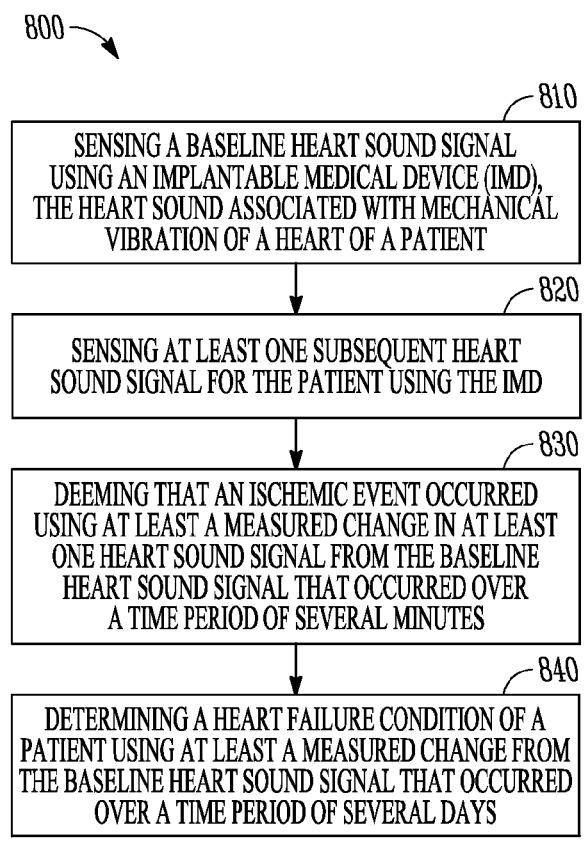
FIG. 8 is a block diagram of another embodiment of a method of detecting ischemia using a heart sound sensor.

FIG. 8 is a block diagram of another embodiment of a method 800 of monitoring one or more mechanical functions of a heart. At 810, a baseline heart sound signal is sensed using an IMD, and at 820, at least one subsequent heart sound signal for the patient is sensed using the IMD. At 830, an occurrence of an ischemic event is inferred if the change in a heart sound signal from the corresponding baseline signal occurs within a time frame of several minutes (e.g., less than fifteen minutes). This is in contrast to a change that is detected by trending of heart sound signal measurements that indicate the change is occurring with a time constant of several hours or days (e.g. more than four hours). If the change from the baseline occurs over the course of hours or days, at 840 the method 800 further includes deeming that the change indicates worsening of a heart failure condition of the patient. In some examples, the method 800 further includes activating the same alarm as an ischemic event alarm, or a different alarm to indicate the heart failure condition.

Figure 9:
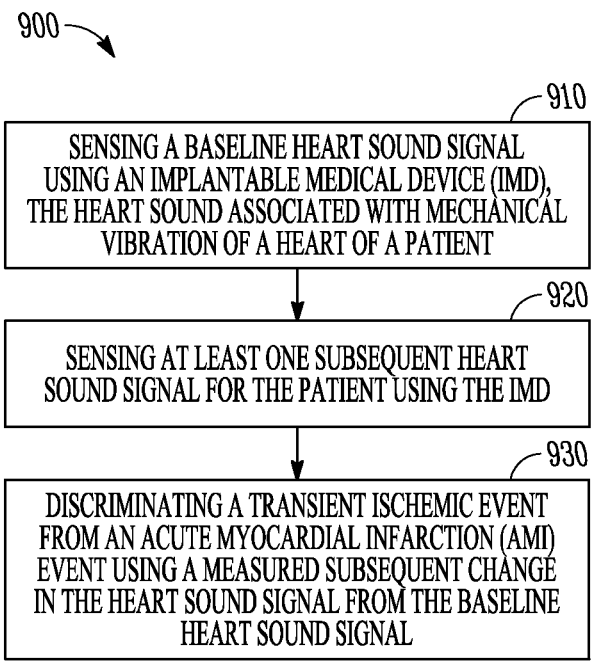
FIG. 9 is a block diagram of another embodiment of a method of detecting ischemia using a heart sound sensor.

FIG. 9 is a block diagram of another embodiment of a method 900 of monitoring one or more mechanical functions of a heart. At 910, a baseline heart sound signal is sensed using an IMD, and at 920, at least one subsequent heart sound signal for the patient is sensed using the IMD. At 930, a transient ischemic event is discriminated from an AMI event using a measured subsequent change in the heart sound signal from the baseline heart sound signal. In some method examples, discriminating a transient ischemic event from an AMI event includes discriminating based on the duration of the measured subsequent change from the established baseline heart sound signal. A longer duration indicates AMI while a short duration indicates a transient event. In some examples, discriminating a transient ischemic event from an AMI event includes discriminating based on the measured amplitude of a subsequent change from the established baseline heart sound signal. A large amplitude change is likely to indicate an AMI event, while a small amplitude change is likely to indicate a transient ischemic event. In some examples, discriminating a transient ischemic event from an AMI event includes discriminating based on a temporal relationship of a sensed event indicated by a sensed cardiac signal and the measured subsequent change in the heart sound signal from the established baseline heart sound signal. An event indicated by both the cardiac signal change and the heart sound change is more likely to be an AMI event if the cardiac signal change goes away but the heart sound change remains. An event that is indicated by a cardiac signal change but occurs without a corresponding change in a heart sound signal is likely to be a transient ischemic change.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A method of operating a medical device system, the method comprising:
   sensing a heart sound signal using an implantable medical device of the medical device system, wherein a heart sound is associated with mechanical vibration of a heart of a subject;
   establishing a baseline value of a characteristic of at least one heart sound in the heart sound signal;
   deeming that an ischemic event occurred using at least a measured subsequent change in the heart sound characteristic from the established baseline value of the heart sound characteristic;
   discriminating a transient ischemic event from an acute myocardial infarction (AMI) using the measured subsequent change in the heart sound characteristic from the established baseline value of the heart sound characteristic; and
   generating, by the medical device system, an indication of the ischemic event or AMI and providing the indication to a user or process.

2. The method of claim 1, wherein the heart sound characteristic includes at least one of:
   an amplitude of a first heart sound of the heart sound signal normalized with respect to an amplitude of a second heart sound; and
   an amplitude of the first heart sound of the heart sound signal normalized with respect to a measured power of the heart sound signal measured during systole.

3. The method of claim 1, wherein the heart sound characteristic includes at least one of:
   a power spectrum of the heart sound of the heart sound signal;
   a frequency of occurrence of a heart sound in the heart sound signal; and
   a duration of an occurrence of the heart sound in the heart sound signal.

4. The method of claim 1,
   wherein establishing a baseline value of a heart sound characteristic includes establishing an amplitude baseline of at least one of an S1 or S2 heart sound; and
   wherein deeming that an ischemic event occurred includes deeming that an ischemic event occurred using a detected decrease in the at least one of the S1 or S2 heart sound from the established baseline amplitude.

5. The method of claim 1, wherein the heart sound characteristic includes a ratio that includes an S3 heart sound amplitude and an S4 heart sound amplitude.

6. The method of claim 1, wherein deeming that an ischemic event occurred is inferred at least in part by detecting, in association with exercise of the subject, a merging of an S3 heart sound and an S4 heart sound in the heart sound signal.

7. The method of claim 1, including:
   sensing an electrical cardiac signal using the medical device and establishing a baseline for the electrical cardiac signal, and
   wherein discriminating a transient ischemic event from an AMI includes discriminating the transient ischemic event from the AMI using a temporal relationship of a detected change in the cardiac signal from the cardiac signal baseline and a detected change in the heart sound characteristic.

8. The method of claim 7, wherein discriminating a transient ischemic event from an AMI includes discriminating a transient ischemic event from an AMI using a sequence of the detected change in the cardiac signal and the detected change in the heart sound characteristic.

9. The method of claim 7, wherein discriminating a transient ischemic event from an AMI includes discriminating a transient ischemic event from an AMI when detecting a change in the cardiac signal that is temporary and detecting a change in the heart sound characteristic that persists.

10. The method of claim 1, including:
    sensing an electrical cardiac signal using the medical device and establishing a baseline for the electrical cardiac signal;
    assigning a first weight to the measured change in the heart sound characteristic and a second weight to a measured change in the electrical cardiac signal from the established baseline electrical cardiac signal; and
    discriminating a transient ischemic event from an AMI using the measured change in the heart sound characteristic, a measured change in the electrical cardiac signal from the established baseline for the electrical cardiac signal, and the assigned weights.

11. A system comprising:
    an implantable medical device (IMD) comprising:
       an implantable heart sound sensor configured to sense a heart sound signal representative of at least one heart sound, wherein the heart sound is associated with mechanical activity of a patient's heart;
       a heart sound sensor interface circuit coupled to the heart sound sensor to produce the heart sound signal; and
       a signal analyzer circuit coupled to the heart sound sensor interface circuit, wherein the signal analyzer circuit is configured to:
          establish a baseline value of a characteristic of at least one heart sound in the heart sound signal;
          deem that an ischemic event occurred using at least a measured subsequent change in the heart sound characteristic from the established baseline value of the heart sound characteristic;
          discriminate a transient ischemic event from an AMI using the measured subsequent change in the heart sound characteristic from the established baseline value of the heart sound characteristic; and
          provide an indication of the ischemic event or AMI to a user or process.

12. The system of claim 11, wherein the signal analyzer circuit is configured to:
    establish a baseline value of at least one of:
       an amplitude of a first heart sound of the heart sound signal normalized with respect to an amplitude of a second heart sound; and
       an amplitude of the first heart sound of the heart sound signal normalized with respect to a measured power of the heart sound signal measured during systole; and
    deem that an ischemic event occurred using a measured subsequent change in the established baseline value.

13. The system of claim 11, wherein the signal analyzer circuit is configured to:
    establish a baseline value of at least one of:
       a power spectrum of the heart sound of the heart sound signal;

a frequency of occurrence of a heart sound in the heart sound signal; and a duration of an occurrence of the heart sound in the heart sound signal; and deem that an ischemic event occurred using a measured subsequent change in the established baseline value.

14. The system of claim 11, wherein the signal analyzer circuit is configured to:

establish a baseline value of an amplitude of at least one of an S1 or S2 heart sound; and deem that an ischemic event occurred using a detected decrease in the amplitude of the at least one of the S1 or S2 heart sound from the established baseline amplitude value.

15. The system of claim 11, wherein the signal analyzer circuit is configured to:

establish a baseline value of a ratio including amplitudes of an S3 and S4 heart sound; and deem that an ischemic event occurred using a detected change in the ratio from the established baseline amplitude value.

16. The system of claim 11, wherein the signal analyzer circuit is configured to deem that an ischemic event occurred at least in part by detecting a merging of an S3 and an S4 heart sound in the heart sound signal in association with exercise of the subject.

17. The system of claim 11, including:

an implantable cardiac signal sensing circuit communicatively coupled to the signal analyzer circuit, wherein the implantable cardiac signal sensing circuit is configured to produce an electrical cardiac signal representative of cardiac activity of the patient, wherein the signal analyzer circuit is configured to:

establish a baseline cardiac signal and detect a change in the cardiac signal from the established baseline cardiac signal; and discriminate the transient ischemic event from AMI using a temporal relationship of the detected change in the cardiac signal and a detected change in the heart sound characteristic.

18. The system of claim 17, wherein the signal analyzer circuit is configured to discriminate the transient ischemic event from AMI using a sequence of the detected change in the cardiac signal and the detected change in the heart sound characteristic.

19. The system of claim 17, wherein the signal analyzer circuit is configured to discriminate the transient ischemic event from AMI when detecting a temporary change in the cardiac signal and a persistent change in the heart sound characteristic.

20. The system of claim 11, including:

an implantable cardiac signal sensing circuit communicatively coupled to the signal analyzer circuit, wherein the implantable cardiac signal sensing circuit is configured to produce an electrical cardiac signal representative of cardiac activity of the patient, and wherein the signal analyzer circuit is configured to:

assign a first weight to the measured change in the heart sound characteristic and a second weight to a measured change in the electrical cardiac signal from the established baseline electrical cardiac signal; and discriminate a transient ischemic event from an AMI using the measured change in the heart sound characteristic, a measured change in the electrical cardiac signal from the established baseline for the electrical cardiac signal, and the assigned weights.

* * * * *